US008592409B2

(12) United States Patent
Claremon et al.

(10) Patent No.: US 8,592,409 B2
(45) Date of Patent: Nov. 26, 2013

(54) CYCLIC CARBAZATE AND SEMICARBAZIDE INHIBITORS OF 11β-HYDROXYSTEROID DEHYDROGENASE 1

(75) Inventors: David A. Claremon, Maple Glen, PA (US); Linghang Zhuang, Chalfont, PA (US); Yuanjie Ye, Ambler, PA (US); Suresh B. Singh, Kendall Park, NJ (US); Colin M. Tice, Ambler, PA (US); Salvacion Cacatian, West Conshohocken, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 205 days.

(21) Appl. No.: 12/863,634

(22) PCT Filed: Jan. 21, 2009

(86) PCT No.: PCT/US2009/000421
§ 371 (c)(1),
(2), (4) Date: Oct. 5, 2010

(87) PCT Pub. No.: WO2009/094169
PCT Pub. Date: Jul. 30, 2009

(65) Prior Publication Data
US 2011/0112082 A1      May 12, 2011

Related U.S. Application Data

(60) Provisional application No. 61/062,147, filed on Jan. 24, 2008.

(51) Int. Cl.
*C07D 265/10* (2006.01)
*A61K 31/417* (2006.01)

(52) U.S. Cl.
USPC ........................... 514/228.8; 544/96; 544/97

(58) Field of Classification Search
USPC .................................. 544/96, 97; 514/228.8
See application file for complete search history.

(56) References Cited

U.S. PATENT DOCUMENTS

| 3,341,538 A | 9/1967 | Block et al. |
| 3,378,587 A | 4/1968 | Reinhardt |
| 3,681,349 A | 8/1972 | Schwan et al. |
| 3,703,529 A | 11/1972 | Frederick et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |

(Continued)

FOREIGN PATENT DOCUMENTS

DE     1801556 A1    5/1970
DE   2 105 743 A1    8/1972

(Continued)

OTHER PUBLICATIONS

Chalmers (TiPS vol. 17, pp. 166-172 Apr. 1996).*
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine—Lewis Base Complex", Journal of Heterocyclic Chemistry, vol. 24, 1987, pp. 361-363.
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.

(Continued)

*Primary Examiner* — Kahsay T Habte
(74) *Attorney, Agent, or Firm* — McCarter & English LLP; Steven G. Davis; Michael J. DeGrazia

(57) ABSTRACT

This invention relates to novel compounds of the Formula (I), (Ia), (Ic), (Ie), (If), (Ig), (Ih), (Ii), pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to cortisol in a cell.

16 Claims, No Drawings

(56) References Cited

U.S. PATENT DOCUMENTS

| | | |
|---|---|---|
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 2 108 954 A1 | 9/1972 |
| DE | 2 229 695 A1 | 1/1974 |
| DE | 23 38 369 A1 | 2/1975 |
| DE | 23 54 002 A1 | 5/1975 |
| DE | 2 411 382 A1 | 9/1975 |
| DE | 2 437 610 A1 | 2/1976 |
| DE | 2 828 039 A1 | 1/1980 |
| DE | 19918725 A1 | 10/2000 |
| DE | 19929348 A1 | 12/2000 |
| DE | 100 34 623 A1 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0 847 275 A1 | 6/1998 |
| EP | 0928789 A1 | 7/1999 |
| EP | 1156049 A | 11/2001 |
| EP | 1270724 A2 | 1/2003 |
| EP | 1801098 A1 | 6/2007 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| JP | 2011519374 A | 7/2011 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | 96/37494 A1 | 11/1996 |
| WO | 97/77889 A1 | 3/1997 |
| WO | 98/22462 A1 | 3/1997 |
| WO | WO 97/36605 | 10/1997 |

(56) References Cited

FOREIGN PATENT DOCUMENTS

| | | |
|---|---|---|
| WO | WO 98/57940 | 12/1998 |
| WO | WO 99/05125 | 2/1999 |
| WO | WO 99/06395 | 2/1999 |
| WO | 009107 A2 | 2/2000 |
| WO | WO 01/00595 A1 | 1/2001 |
| WO | 0113917 A1 | 3/2001 |
| WO | WO 01/44200 A2 | 6/2001 |
| WO | WO 2001/055063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | 03/097608 A2 | 11/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | 2004056745 A2 | 7/2004 |
| WO | 2004/046137 A1 | 10/2004 |
| WO | 2004/089896 A1 | 10/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | 2005116002 A2 | 12/2005 |
| WO | WO 2005/113525 A1 | 12/2005 |
| WO | 2006002349 A1 | 1/2006 |
| WO | WO 2006/003494 A2 | 1/2006 |
| WO | 2006017443 | 2/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | 2006/109056 A1 | 10/2006 |
| WO | WO 2006/104280 A | 10/2006 |
| WO | WO 2007/008529 A2 | 1/2007 |
| WO | 2007/022371 A2 | 2/2007 |
| WO | 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | 2007/076055 A2 | 7/2007 |
| WO | 2007/124337 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | 2007101270 A1 | 9/2007 |
| WO | 2007103719 A2 | 9/2007 |
| WO | WO 2007/109456 A2 | 9/2007 |
| WO | WO 2007/118185 A2 | 10/2007 |
| WO | 2007/127763 A2 | 11/2007 |
| WO | 2007123853 A2 | 11/2007 |
| WO | WO 2007/124254 | 11/2007 |
| WO | WO 2007/124329 A | 11/2007 |
| WO | WO 2007/127693 A | 11/2007 |
| WO | WO 2008/000951 | 1/2008 |
| WO | 2008024497 A2 | 2/2008 |
| WO | WO 2008/031227 A1 | 3/2008 |
| WO | WO 2008/036715 A1 | 3/2008 |
| WO | 2008/046578 A2 | 4/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | 2009020140 A1 | 2/2009 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | 2009/107664 A1 | 9/2009 |
| WO | 2009108332 A1 | 9/2009 |
| WO | WO 2009/117109 | 9/2009 |
| WO | 2009131669 A2 | 10/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | 2010/010150 A1 | 1/2010 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | 2010089303 A1 | 8/2010 |
| WO | WO 2010/091067 | 8/2010 |
| WO | 2010104830 A1 | 9/2010 |
| WO | WO 2010/127237 | 11/2010 |
| WO | 2010/139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011/057054 A1 | 5/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.

(56) References Cited

OTHER PUBLICATIONS

Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.
Zhurnal Organicheskoi Khimii, 1978, vol. 14(5), pp. 1092-1094.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
International Search Report—(PCT/US2010/023021) Date of Mailing Aug. 5, 2010.
Anderson, (Chem and Biol 10:787-797, 2003).
Bosch et al.: Heterocycles 1980, 14, p. 1983-1988.
CA 1267843-31-1, (Aug. 10, 2009). cited by other.
CA 154:284276, (Mar. 17, 2011). cited by other.
Caplus-133:4656—Anantanarayan, A. el. al., "Preparation of heteroarylpyrazoles as P38 kinase inhibitors". 2000.
Caplus-147:134403, Hembrough, TA, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
Chemical Abstracts, Registry Number: 351443-37-3 (Available on Aug. 15, 2001.).
Claremon et al. CAS: 150:214405, 2009.
Database CA [Online], Chemical Abstracts Service, Fukushima et al., "Preparation of Imidazolidinone Derivatives as 11.beta.-HSD1 Inhibitors", 2007, XP 002531878. cited by other.
DeMarinis R.M. et.al. Journal of Medicinal Chemistry 1981, vol. 24, No. 12, pp. 1432-1437.
Examiner Interview Summary dated May 2, 2011, in U.S. Appl. No. 12/741,522 (U.S. Patent No. 8,138,178).
Gavezzotti, "Are Crystal Structures Predictable?", Accounts of Chemical Research, 1994, vol. 27, pp. 309-314. cited by other.
Gutkowska et al.: Acta Polonaie Pharmaceutica 1987, 39, p. 411-414.
Gutkowska et al.: Acta Poloniae Pharmaceutica 1986, 43, p. 403-405.

(56) References Cited

OTHER PUBLICATIONS

Gutkowska et al.: Acta Poloniae Pharmaceutica, 1982, vol. 39, p. 61-64.
Harno et.al. Trends in Endocrinology and Metabolism, Elsevier Science Publishing, New York 2010, vol. 21, No. 10, pp. 619-627.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report and Written Opinion for PCT/EP2009/059509, mailed Feb. 9, 2009.
International Search Report and Written Opinion for PCT/US2012/050679 mailed Oct. 31, 2012.
International Search Report for PCT/EP2009/063913 mailed May 6, 2010.
Ma et al.: Synthesis 2007, p. 161-163.
Ma et al.: Tetrahedron 2007, 63, p. 7523-7531.
Morissette et al. Advanced Drug Deliery Reviews 2004, 56, 275-300.
Office Action dated Apr. 3, 2012 for corresponding application U.S. Appl. No. 13/318,271.
Office Action dated Jun. 14, 2012 for corresponding U.S. Appl. No. 13/347,784.
Office Action dated May 3, 2012 for corresponding U.S. Appl. No. 13/347,799.
Office Action for U.S. Appl. No. 12/741,522 (U.S. Patent No. 8,138,178), date of mailing Dec. 15, 2010.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Olesen et al.: Current Opin Drug Dis Dev, 2001, vol. 4, No. 4, p. 471-478.
Rosenstock et.al. Diabetes Care Jul. 2010, LNKDPUBMED: 20413513, vol. 33, No. 7, pp. 1516-1522.
Souillac et al., Characterization of Delivery Systems, Differential Scanning Calorimetry, pp. 217-218 (in Encyclopedia of Controlled Drug Delivery, 1999, John Wiley & Sons, pp. 212-227).
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968). cited by other.
Taddayon et.al. Expert opinion on Investigational Drugs, Ashley Publication Ltd. 2003, vol. 12, No. 3, pp. 307-324.
Thiel (Nature Biotechnol 2:513-519, 2004).
Thornber et al.: Chem Soc Rev, 1979, vol. 8, p. 563-580.
Vidic et al.: Chem. Ber. 1976, 109, p. 2657-2669.
Vippagunta, et al., "Crystalline Solids", Advanced Drug Deliver Reviews, 2001, vol. 48, pp. 3-26. cited by other.
Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
Yokoyama et al.: J. Med. Chem. 1979, 22, p. 537-553.

Database CA [Online], Chemical Abstracts Service, Fukushima et al., "Preparation of Imidazolidinone Derivatives as 11.beta.-HSD1 Inhibitors", 2007, XP 002531878.
Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.
Evans, B.E. et al., "Orally active, nonpeptide osytocin antagonists". Journal of Medicinal Chemistry, American Chem. Soc., Vo. 35, No. 21, Oct. 15, 1992, pp. 3919-3927.
Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, pp. 5731-5741.
Aluri, B.R. et al., "Bulky n-Substituted 1,3-Benzazaphospholes: Access via Pd-Catalyzed C-N, and C-P, Cross Coupling, Lithiation, and Conversion to Novel P=C PtBu2 Hybrid Ligands". Inorganic Chemistry, 2008, 47, p. 6900-6912.
Aluri, B.R. et al., "Sterically and Polarity-Controlled Reactions of tBuLi with P=CH-NR Heterocycles: Novel Heterocyclic P-and P,O-Ligands and Preliminary Tests in Transition-Metal Catalysis", Chem. Eur. Journal, vol. 14, 2008, p. 4328-4335.
Fandrick, DR. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.
International Search Report and Written Opinion for PCT/EP12009/059496 mailed Nov. 17, 2009.
International Search Report and Written Opinion for PCT/EP2010/051262 mailed May 3, 2010.
International Search Report and Written Opinion for PCT/EP2011/060386 mailed Sep. 16, 2011.
International Search Report and Written Opinion for PCT/US2010/054912 mailed Mar. 16, 2011.
International Search Report for PCT/EP2011/068938 mailed Mar. 27, 2012.
Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.
Senanayake, C. Presentation: "Timely Chemical Process Research is a Critical Part for Efficient Drug Development". 4th Siegfried Symposium, Sep. 23, 2010, p. 1-91, Retrieved from Internet: URL: http://www.siegfried/ch/fileadmin/User2/Bilder/Fotogalerien/Symposium_2010/Award_Talk_Senanayake.pdf. Retrieved on Feb. 23, 2010.
Tang, W. et al., "Novel and Efficient Chiral Bisphosphorus Ligands for Rhodium-Catalyzed Asymmetric Hydrogenation". Organic Letters, 2010, vol. 12, No. 5, pp. 1104-1107.
Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.
Worthy, AD. et al., "Regioselective Hydroformylation of Sulfonamides using a Scaffolding Ligand". Organic Letters, 2009, vol. 11, No. 13—p. 2764-2767.

\* cited by examiner

CYCLIC CARBAZATE AND SEMICARBAZIDE INHIBITORS OF 11β-HYDROXYSTEROID DEHYDROGENASE 1

RELATED APPLICATIONS

This application is the U.S. National Phase of PCT/US2009/000421, filed Jan. 21, 2009, which claims the benefit of U.S. Provisional Application Ser. No. 61/062,147, filed Jan. 24, 2008, the entire teachings of which are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), $4^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Harm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated Iop can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or a pharmaceutically acceptable salt or prodrug thereof, are effective inhibitors of 11β-HSD1. Formula I and its constituent members are defined herein as follows:

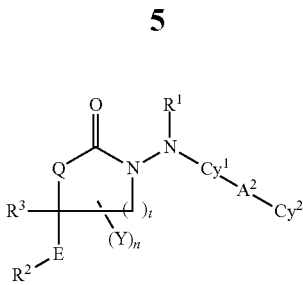

I $R^1$ is (a) hydrogen or (b) is selected from $(C_1-C_6)$alkyl, $(C_2-C_6)$alkenyl, $(C_2-C_6)$alkynyl or $(C_1-C_3)$alkoxy$(C_1-C_3)$ alkyl, wherein each is optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, aryl, cycloalkyl, heterocyclyl, heteroaryl, arylamino and heteroarylamino;

$Cy^1$ is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino $(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$ heterocyclylcarbonyl, $(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

t is 1, 2 or 3;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$ cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$R^3$ is selected from hydrogen, $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4O)_2P(=O)NR^4-$, $R^4OS(=O)_2NR^4-$, $(R^4)_2NS(=O)_2-$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

Q is O or $NR^5$;

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

$R^5$ is H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

Another embodiment of the present invention is a pharmaceutical composition comprising: i) a pharmaceutically acceptable carrier or diluent; and ii) a compound of Formula I, Ia, Ib, Ic, Id, Ie, If, Ig, Ih or Ii, or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas I, Ia, Ib, Ic, Id, Ie, If, Ig, Ih or Ii, or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, Ia, Ib, Ic, Id, Ie, If, Ig, Ih or Ii, or a pharmaceutically acceptable salt, enantiomer or diastereomer thereof.

Another embodiment of the invention is the use of a compound of Formulas I, Ia, Ib, Ic, Id, Ie, If, Ig, Ih or Ii, or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas I, Ia, Ib, Ic, Id, Ie, If, Ig, Ih or Ii, or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, Ia, Ib, Ic, Id, Ie, If, Ig, Ih or Ii, or a pharmaceutically acceptable salt, enantiomer or diastereomer thereof for use in inhibiting 11β-HSD1 activity in a mammal in need of such treatment.

Another embodiment of the invention is a compound of Formulas I, Ia, Ib, Ic, Id, Ie, If, Ig, Ih or Ii, or a pharmaceutically acceptable salt, enantiomer or diastereomer thereof for use in for treating a subject with a disease associated with the activity or expression of 11β-HSD1.

The present invention further provides methods of inhibiting 11β-HSD1 by contacting 11β-HSD1 with a compound of Formula I, Ia, Ib, Ic, Id, Ie, If, Ig, Ih or Ii of the invention.

The present invention further provides methods of inhibiting or reducing the conversion of cortisone to cortisol in a subject in need of such treatment by administering to the subject an effective amount of a compound of Formula I, Ia, Ib, Ic, Id, Ie, If, Ig, Ih or Ii of the invention.

The present invention further provides methods of inhibiting or reducing production of cortisol in a subject in need of such treatment by administering to the subject an effective amount of a compound of Formula I, Ia, Ib, Ic, Id, Ie If, Ig, Ih or Ii of the invention.

The present invention further provides methods of increasing insulin sensitivity in a subject in need thereof using a compound of Formula I, Ia, Ib, Ic, Id, Ie, If, Ig, Ih or Ii of the invention.

DETAILED DESCRIPTION OF THE INVENTION

Another embodiment is a compound of Formula I or any one of Formulas Ia-i wherein:

$Cy^1$ is phenyl, naphthyl, indanyl, tetrahydronaphthalene, 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, (all of which may be optionally substituted), cyclopropyl, cyclobutyl, cyclopentyl, cyclohexyl, cycloheptyl, cyclooctyl, pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide or isothiazolidine 1,1-dioxide, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

E is a bond or $(C_1-C_3)$alkylene optionally substituted with 1 to 4 groups independently selected from methyl, ethyl, trifluoromethyl or oxo;

$R^3$ is selected from hydrogen, $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo) and heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

and the remainder of the variables are as described above for Formula I or below for any one of Formulas Ia-Ii;

or a pharmaceutically acceptable salt, enantiomer or diastereomer thereof.

Another embodiment is a compound of Formula I or any one of Formulas Ia-i wherein:

$R^1$ (for Formulas I, Ia-d and Ig) is hydrogen, methyl or ethyl;

$Cy^1$ (for Formulas I, Ia-d and Ig) is phenyl, cyclopropyl, cyclohexyl, pyrrolidinyl, pyridyl, N-oxo-pyridyl, thiazolyl or pyrimidinyl, each optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;

$A^2$ (for Formulas I, Ia-d and Ie-g) is a bond, O, $OCH_2CO$ or C=O;

$Cy^2$ (for Formulas I, Ia-d and Ie-g) is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl or 2-oxo-1,2-dihydropyridyl, each optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

n (for Formula I and Ia-d) is 0;

t (for Formulas I and Ie-i) is 1, 2 or 3;

E (for Formulas I, Ia-d, Ie-f and Ih-i) is a bond or $CH_2$;

$R^2$ (for Formulas I, Ia-d, Ie-f and Ih-i) is isopropyl, thienyl, phenyl, or pyridyl, each optionally substituted with halo, methyl, methylthio or (4-morpholino)methyl;

$R^3$ (for Formulas I, Ia-d and Ie-i) is hydrogen, methyl, ethyl, propyl, butyl, vinyl, allyl or ethoxyethyl, each optionally substituted with up to two groups independently selected from HO—, MeO—, $H_2N$—, $MeC(=O)NH$—, $MeS(=O)_2NH$—, $H_2NC(=O)$—, $MeNHC(=O)$—, $HO_2C$—, $(HO)_2P(=O)O$—, $H_2NS(=O)_2O$—, $H_2NS(=O)_2NH$—, $MeNHC(=O)NH$—, $MeNHC(=O)O$-oxo, cyano, $HO_2C$—, $HOCH_2CH_2NH$—, 4-morpholino, $HOCH_2C(=O)NH$—, $H_2NCH_2C(=O)NH$—, $EtNHC(=O)NH$, $MeOC(=O)NH$—, $MeNHC(=NC=N)NH$—, Me-, MeS—, $MeSO_2$-$MeSO_2N(Me)$-, $MeS(=O)_2NHC(=O)$—, imidazolylamino-, imidazolyl, tetrazolyl, $H_2NCONH$—, $H_2NCO_2$—, $HOCH_2CH_2O$—, MeNH—, $Me_2N$— and MeCONMe;

Q (for Formulas I and Ie-i) is O or $NR^5$;

$R^5$ (for Formulas I and Ie-i) is hydrogen or methyl;

or a pharmaceutically acceptable salt, enantiomer or diastereomer thereof.

Another embodiment is a compound of Formula Ia:

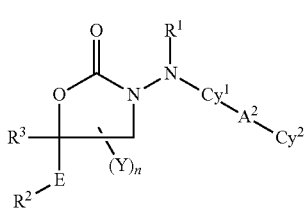

Ia wherein $A^2$, $Cy^1$, $Cy^2$, E, n, Y, $R^1$, $R^2$, and $R^3$ are as defined for Formula I above; or a pharmaceutically acceptable salt, enantiomer or diastereomer thereof.

Another embodiment is a compound of Formula Ib:

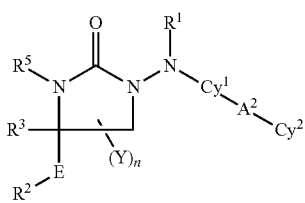

Ib wherein $A^2$, $Cy^1$, $Cy^2$, E, n, Y, $R^1$, $R^2$, $R^3$ and $R^5$ are as defined as for Formula I above; or a pharmaceutically acceptable salt, enantiomer or diastereomer thereof.

Another embodiment is a compound of Formula Ic:

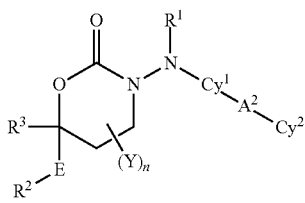

Ic wherein $A^2$, $Cy^1$, $Cy^2$, E, n, Y, $R^1$, $R^2$, and $R^3$ are as defined for Formula I above; or a pharmaceutically acceptable salt, enantiomer or diastereomer thereof.

Another embodiment is a compound of Formula Id:

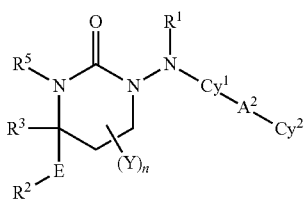

Id wherein $A^2$, $Cy^1$, $Cy^2$, E, n, Y, $R^1$, $R^2$, $R^3$ and $R^5$ are as defined for Formula I above; or a pharmaceutically acceptable salt, enantiomer or diastereomer thereof.

Another embodiment is a compound of Formula Ie:

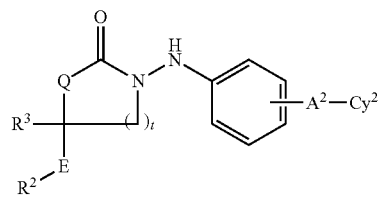

Ie wherein $A^2$, $Cy^2$, E, t, Q, $R^2$, and $R^3$ are as defined for Formula I above; or a pharmaceutically acceptable salt, enantiomer or diastereomer thereof.

Another embodiment is a compound of Formula If:

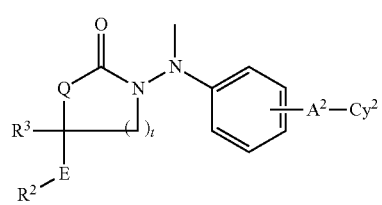

If wherein $A^2$, $Cy^2$, E, t, Q, $R^2$, and $R^3$ are as defined for Formula I above; or a pharmaceutically acceptable salt, enantiomer or diastereomer thereof.

Another embodiment is a compound of Formula Ig:

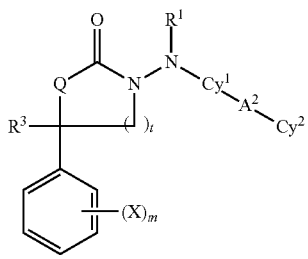

Ig wherein $R^1$, $Cy^1$, $A^2$, $Cy^2$, t, Q, and $R^3$ are as defined for Formula I above; m is 0, 1, 2, 3 or 4; and substituents X are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfonyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof. In a specific embodiment, $A^2$-$Cy^2$ is meta or para to the carbon atom bonded to N.

Another embodiment is a compound of Formula Ih:

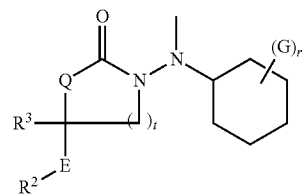

Ih wherein E, t, Q, $R^2$, and $R^3$ are as defined for Formula I above, r and s are independently 0, 1, 2, 3 or 4; and $G^1$ and $G^2$ are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

Another embodiment is a compound of Formula Ii:

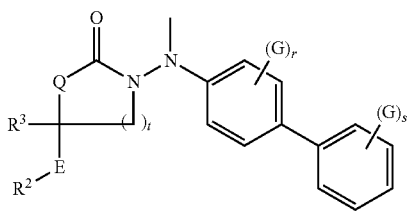

Ii wherein E, t, Q, $R^2$, and $R^3$ are as defined for Formula I above, r is 0, 1, 2, 3 or 4; and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

In certain specific embodiments of the invention, the variables in the above-described structural formulas have the following values:

$R^1$ is (a) hydrogen or (b) is selected from ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl, wherein each is optionally substituted with up to four groups independently selected from fluorine, cyano, oxo, $R^4$, $R^4O$—, ($R^4$)$_2$N—, $R^4O_2C$—, $R^4S$, $R^4S$(=O)—, $R^4S$(=O)$_2$—, $R^4C$(=O)$NR^4$—, ($R^4$)$_2NC$(=O)—, ($R^4$)$_2NC$(=O)O—, ($R^4$)$_2NC$(=O)$NR^4$—, $R^4OC$(=O)$NR^4$—, ($R^4$)$_2NC$(=NCN)$NR^4$—, ($R^4O$)$_2P$(=O)O—, ($R^4O$)$_2P$(=O)$NR^4$—, $R^4OS$(=O)$_2NR^4$—, ($R^4$)$_2NS$(=O)$_2O$—, ($R^4$)$_2NS$(=O)$_2NR^4$—, $R^4S$(=O)$_2NR^4$—, $R^4S$(=O)$_2NHC$(=O)—, $R^4S$(=O)$_2NHC$(=O)O—, $R^4S$(=O)$_2NHC$(=O)

NR⁴—, R⁴OS(=O)₂NHC(=O)—, R⁴OS(=O)₂NHC(=O)O—, R⁴OS(=O)₂NHC(=O)NR⁴—, (R⁴)₂NS(=O)₂NHC(=O)—, (R⁴)₂NS(=O)₂NHC(=O)O—, (R⁴)₂NS(=O)₂NHC(=O)NR⁴—, R⁴C(=O)NHS(=O)₂—, R⁴C(=O)NHS(=O)₂O—, R⁴C(=O)NHS(=O)₂NR⁴—, R⁴OC(=O)NHS(=O)₂—, R⁴OC(=O)NHS(=O)₂O—, R⁴OC(=O)NHS(=O)₂NR⁴—, (R⁴)₂NC(=O)NHS(=O)₂—, (R⁴)₂NC(=O)NHS(=O)₂O—, (R⁴)₂NC(=O)NHS(=O)₂NR⁴—, aryl, cycloalkyl, heterocyclyl, heteroaryl, arylamino and heteroarylamino. In another alternative, R¹ is (C₁-C₆)alkyl. In another alternative, R¹ is hydrogen, methyl or ethyl. In another alternative, R¹ is methyl or ethyl.

Cy¹ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkythio, (C₄-C₇)cycloalkylalkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl; Alternatively, Cy¹ is phenyl, naphthyl, indanyl, tetrahydronaphthalene, 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, (all of which may be optionally substituted), cyclopropyl, cyclobutyl, cyclopentyl, cyclohexyl, cycloheptyl, cyclooctyl, pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide or isothiazolidine 1,1-dioxide, wherein each is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkythio, (C₄-C₇)cycloalkylalkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl; In another alternative, Cy¹ is optionally substituted aryl or optionally substituted heteroaryl. In another alternative, Cy¹ is optionally substituted phenyl or optionally substituted pyridyl. In another alternative, Cy¹ is optionally substituted phenyl. In yet another specific embodiment, Cy¹ is substituted with fluorine chlorine, bromine, methoxy, methoxycarbonyl, carboxy, or methyl. In yet another specific embodiment, Cy¹ is substituted with fluorine or bromine. In yet another alternative, Cy¹ is phenyl, cyclopropyl, cyclohexyl, pyrrolidinyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino.

A² is (a) a bond, O, S or NR⁴; or (b) (C₁-C₃)alkylene or (C₁-C₂)alkyleneoxy, each of which is optionally substituted with 1 to 4 groups independently selected from methyl, ethyl, trifluoromethyl or oxo; Alternatively, A² is a bond, O, OCH₂CO or C=O; In another alternative, A² is a bond and Cy² is hydrogen. In another alternative, A² is a bond and Cy² is cyclopropyl. In another alternative, A² is a bond and Cy² is optionally substituted aryl or optionally substituted heteroaryl. In another alternative, A² is a bond and Cy² is optionally substituted phenyl or optionally substituted pyridyl. In another alternative, A² is a bond and Cy² is optionally substituted phenyl. In another alternative, A² is a bond and Cy² is substituted with 1 to 4 groups independently selected from chlorine or fluorine. In yet another specific embodiment, $A^2$ is a bond and $Cy^2$ is difluorophenyl.

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkyl-alkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl; Alternatively, $Cy^2$ is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl. In another alternative, $Cy^2$ is optionally substituted phenyl. In another alternative, $Cy^2$ is phenyl optionally substituted with 1-4 groups selected from chlorine and fluorine. In another alternative, $Cy^2$ is difluorophenyl.

t is 1, 2 or 3. In another specific embodiment t is 1. Alternatively, t is 2.

Y is $(C_1-C_6)$alkyl or halo$(C_1-C_6)$alkyl.

n is 0, 1 or 2. Alternatively, n is 0.

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo. Alternatively, E is a bond or $CH_2$. In yet another alternative, E is a bond or $(C_1-C_3)$alkylene optionally substituted with 1 to 4 groups independently selected from methyl, ethyl, trifluoromethyl or oxo.

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl; Alternatively, $R^2$ is isopropyl, thienyl, phenyl, or pyridyl, each optionally substituted with halo, methyl, methylthio or (4-morpholino)methyl. In another alternative, $R^2$ is optionally substituted aryl, optionally substituted heteroaryl or cycloalkyl. In yet another alternative, $R^2$ is optionally substituted phenyl, optionally substituted pyridyl or optionally substituted thienyl. In yet another alternative, $R^2$ is optionally substituted phenyl. In yet another alternative, $R^2$ is fluorophenyl. In yet another alternative, $R^2$ is isopropyl, thienyl, phenyl, or pyridyl, each optionally substituted with halo, methyl, methylthio or (4-morpholino)methyl.

$R^3$ is selected from hydrogen, $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo). Alternatively, $R^3$ is selected from hydrogen, $(C_1-C_6)$alkyl, $(C_2-C_6)$alkenyl, $(C_2-C_6)$alkynyl and $(C_1-C_3)$alkoxy$(C_1-C_3)$ alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl (which in turn may be optionally substituted with alkyl, haloalkyl or oxo) and heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo). In another alternative, $R^3$ is hydrogen. In yet another alternative, $R^3$ is hydroxy$(C_2-C_4)$alkyl. In yet another alternative, $R^3$ is $\omega$-$H_2NCO(C_1-C_3)$alkyl. In yet another alternative, $R^3$ is $(C_1-C_2)$alkoxy$(C_1-C_3)$alkyl. In yet another alternative, $R^3$ is $H_2NSO_2O(C_2-C_4)$alkyl. In yet another alternative, $R^3$ is $H_2NSO_2NH(C_2-C_4)$alkyl. In yet another alternative, $R^3$ is oxo$(C_2-C_4)$alkyl. In yet another specific embodiment, $R^3$ is alkenyl. In yet another alternative, $R^3$ is allyl. In yet another alternative, $R^3$ is MeC$(=O)NH(C_2-C_4)$alkyl. $R^3$ is hydrogen, methyl, ethyl, propyl, butyl, vinyl, allyl or ethoxyethyl, each optionally substituted with up to two groups independently selected from HO—, MeO—, $H_2N$—, MeC$(=O)NH$—, MeS$(=O)_2NH$—, $H_2NC(=O)$—, MeNHC$(=O)$—, $HO_2C$—, $(HO)_2P(=O)O$—, $H_2NS(=O)_2O$—, $H_2NS(=O)_2NH$—, MeNHC$(=O)NH$—, MeNHC$(=O)O$-oxo, cyano, $HO_2C$—, HOCH$_2$CH$_2$NH—, 4-morpholino, HOCH$_2$C$(=O)NH$—, $H_2NCH_2C(=O)NH$—, EtNHC$(=O)NH$, MeOC$(=O)NH$—, MeNHC$(=NC=N)NH$—, Me-, MeS—, MeSO$_2$-MeSO$_2$N(Me)-, MeS$(=O)_2NHC(=O)$—, imidazolylamino-, imidazolyl, tetrazolyl, $H_2NCONH$—, $H_2NCO_2$—, HOCH$_2$CH$_2$O—, MeNH—, Me$_2$N— and MeCONMe.

Q is O or $NR^5$. Alternatively, Q is O. Alternatively, Q is N.

$R^5$ is H, $(C_1-C_6)$alkyl, halo$(C_1-C_6)$alkyl, or hydroxy$(C_1-C_6)$alkyl; Alternatively, $R^5$ is hydrogen or methyl. In one specific embodiment, $R^5$ is hydrogen.

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl.

m is 0, 1, 2, 3 or 4.

X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl.

r and s are independently 0, 1, 2, 3 or 4.

$G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$ alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl.

G is independently selected from fluorine, chlorine, bromine, iodine, cyano, nitro, amino, hydroxy, carboxy, $(C_1-C_6)$ alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$ alkoxy, $(C_3-C_6)$cycloalkoxy, $(C_4-C_7)$cycloalkylalkoxy, halo $(C_1-C_6)$alkoxy, halo$(C_3-C_6)$cycloalkoxy, halo$(C_4-C_7)$ cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$ alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$ cycloalkylalkanesulfinyl, $(C_1-C_6)$alkanesulfonyl, $(C_3-C_6)$ cycloalkanesulfonyl, $(C_4-C_7)$cycloalkylalkanesulfonyl, halo $(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo $(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$ alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$ alkylcarbonylamino, $(C_1-C_6)$alkylcarbonylamino$(C_1-C_6)$ alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$ alkyl, hydroxy$(C_1-C_6)$alkoxy, heteroaryl, amino$(C_1-C_6)$ alkyl, $(C_1-C_6)$alkylamino$(C_1-C_6)$alkyl, di$(C_1-C_6)$alkylamino $(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$ alkylcarbonyl.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo [2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1, 2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. A heterocyclyl can be optionally substituted with 1-4 substituents. Exemplary substituents include alkyl, haloalkyl and oxo.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enatiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

The following abbreviations have the indicated meanings:

| Abbreviation | Meaning |
| --- | --- |
| Boc | tert-butoxy carbonyl or t-butoxy carbonyl |
| (Boc)₂O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC.HCl, EDCl | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH₄ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO₃ | sodium bicarbonate |
| NaN₃ | sodium azide |
| NaOH | sodium hydroxide |
| Na₂SO₄ | sodium sulfate |
| NMM | N-methylmorpholine |
| NMP | N-methylpyrrolidinone |
| Pd₂(dba)₃ | tris(dibenzylideneacetone)dipalladium(0) |
| PE | petroleum ether |
| Quant | quantitative yield |
| Satd | saturated |
| SOCl₂ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et₃N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxyl]pyrrolidin-2,5-dione |
| TFA | trifluoroacetic acid |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthetic Methods

Compounds of Formula I can be prepared by several processes. In the discussion below, $A^2$, $Cy^1$, $Cy^2$, E, Q, $R^1$, $R^2$, $R^3$, $R^5$, Y, n and t have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process, compounds of Formula I, wherein Q is $NR^5$ or O and $R^1$ is not hydrogen, can be prepared by reaction of intermediates of Formula II with reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.

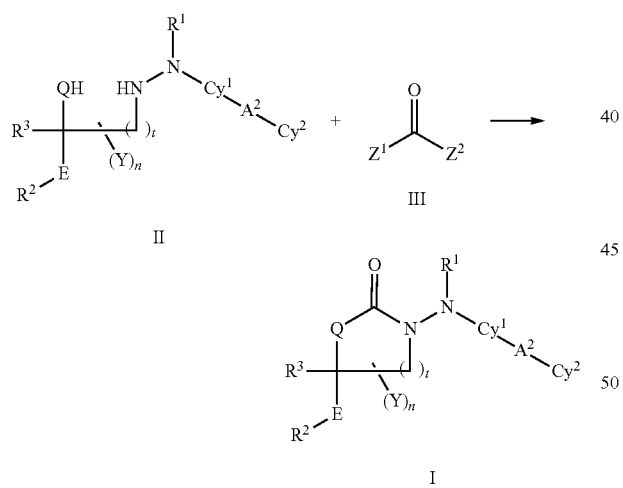

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Intermediates of Formula II, wherein n=0, can be prepared by reduction of hydrazides of Formula IV using a hydride reagent such as $BH_3$.THF solution, $BH_3.Me_2S$ or $LiAlH_4$ in an inert solvent ethereal such as THF or DME at $20°$ C. to $100°$ C. for between 1 h and 48 h:

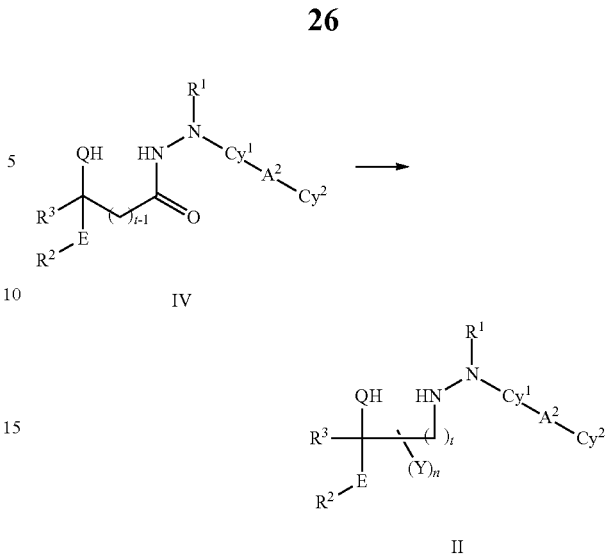

Hydrazide intermediates of Formula IV can be prepared by coupling of α- (t=1), β- (t=2) and γ- (t=3) amino (Q=$NR^5$) and hydroxy (Q=O) acids of Formula V with hydrazines of Formula VI using standard peptide coupling reagents such as EDC in the presence of HOBt and N,N-diisopropylethylamine in an inert solvent such as $CH_2Cl_2$ at $0\text{-}30°$ C. for between 1 h and 24 h:

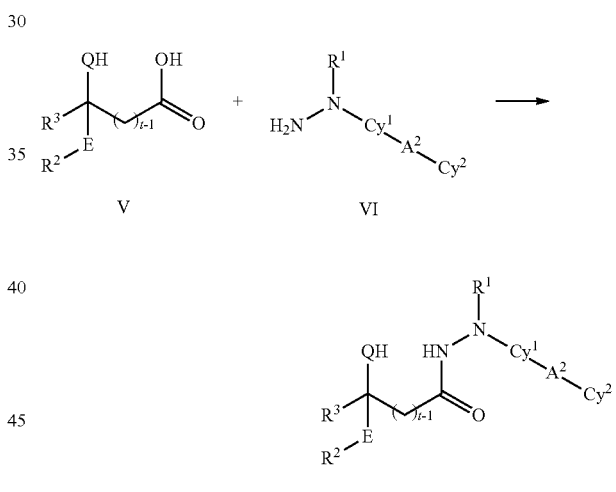

Many α-aminoacids including those of Formula V, wherein t=1 and Q is $NR^5$, are commercially available and methods for their synthesis are widely known in the art. (Smith, M. B. and March, J. "March's Advanced Organic Chemistry" p 1656, 5th Edition, Wiley, New York, N.Y., 2001).

Methods for the synthesis β-aminoacids including those of Formula V, wherein t=2 and Q is $NR^5$, have been reviewed (Enantioselective Synthesis of 3-Amino Acids (2nd Edition) (2005), Publisher: John Wiley & Sons, Inc., Hoboken, N. J). One method for the synthesis of a compound of Formula V, wherein $R^5$ is H and n is O, is the addition of the enolate of an ester of Formula VIII, wherein $R^a$ is ($C_1$-$C_6$)alkyl, to a sulfinylimine of Formula VII to give a compound of Formula IX, followed by ester hydrolysis and removal of the t-butylsulfinyl group:

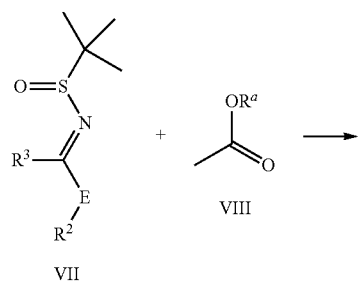

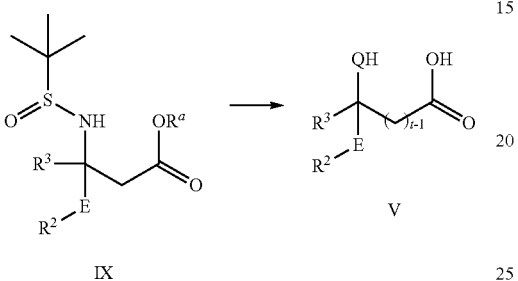

γ-Amino acids of Formula V, wherein t=2 and Q is NR⁵ and R⁵ is H, can be prepared hydrolysis of γ-aminoesters of Formula X, wherein $R^a$ is lower alkyl, with LiOH, NaOH or KOH.

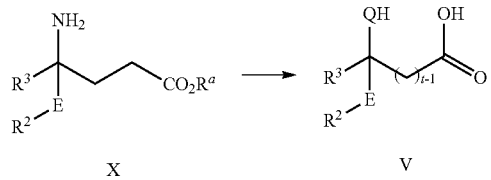

γ-Aminoesters of Formula X, wherein Q is NR⁵ and R⁵ is H, can be prepared by reduction of γ-nitroesters of Formula XI.

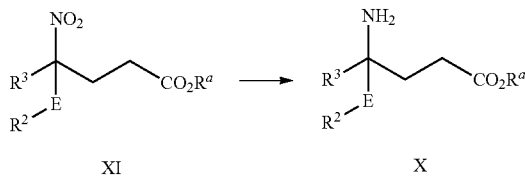

γ-Nitroesters of Formula XI can be prepared by Michael addition of nitro compounds of Formula XII to acrylate esters of Formula XIII.

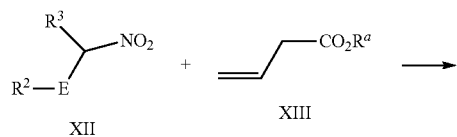

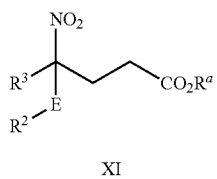

γ-Aminoacids of Formula V, wherein t=2, Q is NR⁵ and R⁵ is H, can also be prepared from homoallyl amines of Formula XIV by hydroboration using a borane such as disiamylborane, followed by oxidation with, for example, Jones reagent.

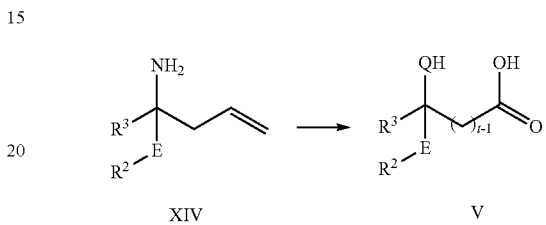

Homoallyl amines of Formula XIV, wherein R⁵ is H, can be prepared by addition of allylmagnesium halides to sulfinylimines of Formula XV, followed by acid treatment to remove the t-butylsulfinyl group.

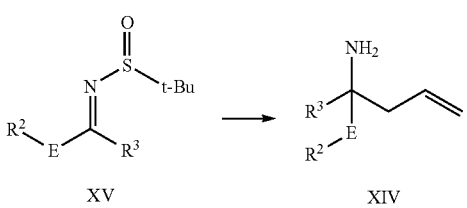

Sulfinylimines of Formula XV can be prepared by reaction of ketones of Formula XVI with 2-methylpropane-2-sulfinamide.

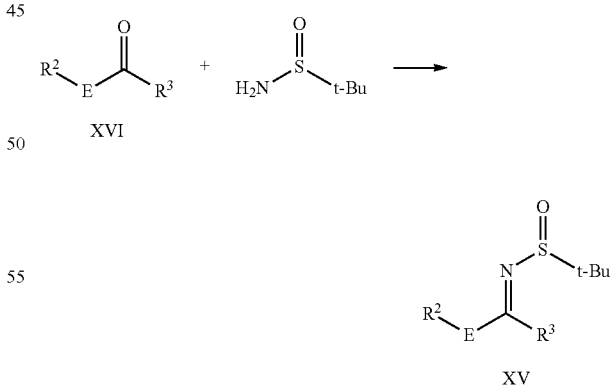

Certain α-hydroxyacids of Formula V, wherein Q is O and t is 1, are commercially available. Additional α-hydroxyacids of Formula V, wherein Q is O and t is 1, can be prepared by diazotization of α-amino acids of Formula XVII using $NaNO_2$ in $H_2SO_4$:

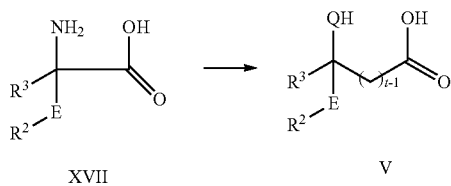

XVII → V

α-Hydroxyacids of Formula V, wherein Q is O and t is 1, can also be prepared from ketones of Formula XVI via cyanohydrins of Formula XVIII:

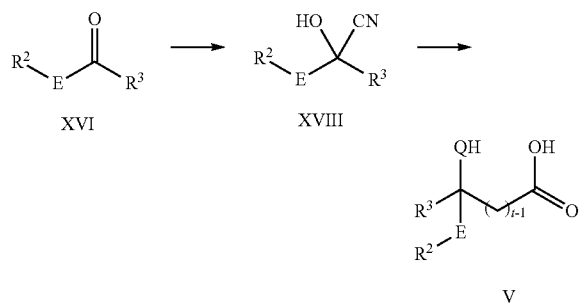

XVI → XVIII → V

Methods for the conversion of ketones to cyanohydrins are described in Smith, M. B. and March, J. "March's Advanced Organic Chemistry" pp 1239-1240, 5$^{th}$ Edition, Wiley, New York, N.Y., 2001. Methods for the hydrolysis of cyanohydrins to α-hydroxyacids are described in Smith, M. B. and March, J. "March's Advanced Organic Chemistry" p 1179, 5$^{th}$ Edition, Wiley, New York, N.Y., 2001

Hydroxyacids of Formula V can also be prepared by oxidation of diols of Formula XIX with for example oxygen in the presence of a catalyst or using sodium chlorite and TEMPO:

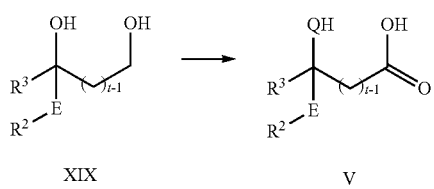

XIX → V

Diols of Formula XIX, wherein t is 1 can be prepared by treatment of olefins of Formula XX with catalytic OsO4 in the presence of N-methylmorpholine-N-oxide.

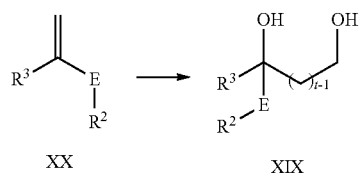

XX → XIX

Olefins of Formula XX are available from ketones of Formula XVI by Wittig reaction with methylenetriphenylphosphorane or by using the Tebbe reagent.

Diols of Formula XIX, wherein t is 1, are available by hydroboration of allyl alcohols of Formula XXI using, for example, disiamylborane. Alternatively, diols of Formula XIX, wherein t is 1, are available by treatment of homoallyl alcohols of Formula XXII with ozone followed by NaBH$_4$.

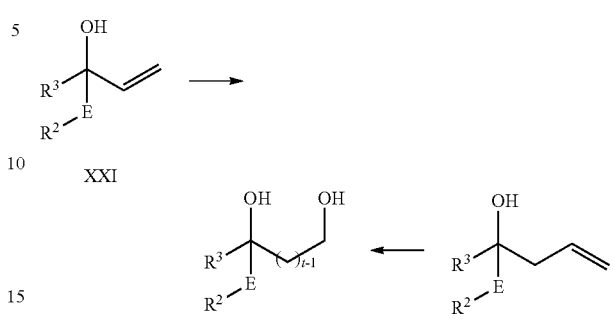

XXI

XIX ← XXII

Allyl alcohols of Formula XXI and homoallyl alcohols of Formula XXII can be prepared by treatment of ketones of Formula XVI with vinylmagnesium halide or allylmagnesium halide respectively.

Diols of Formula XIX, wherein t is 2, can be prepared by hydroboration of homoallyl alcohols of Formula XXII using, for example, disiamylborane.

Hydrazine intermediates of Formula VI, wherein $R^1$ is H and $Cy^1$ is aryl or heteroaryl can be prepared by diazotization of amines of Formula XXIII and reduction of the diazonium salts with, for example, tin(II) chloride.

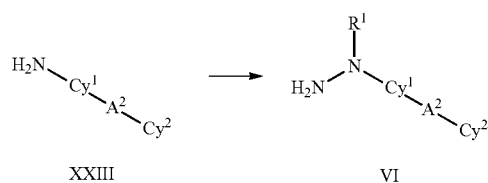

XXIII → VI

Hydrazine intermediates of Formula VI can also be prepared by reduction of nitrosamines of Formula XXXV, using for example LiAlH$_4$ in THF or Na in EtOH. Nitrosamines of Formula XXXIV can be prepared from amines of Formula XXIV by reaction with NaNO$_2$ in the presence of acid.

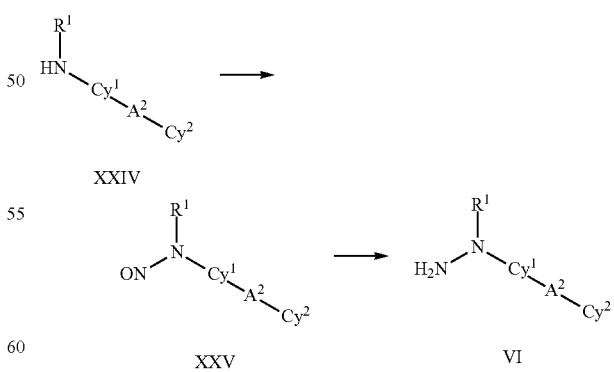

XXIV

XXV → VI

Hydrazine intermediates of Formula VI can also be prepared by amination of amines of Formula)(XXIV with, for example, chloramine or hydroxylamine-O-sulfonic acid.

Hydrazine intermediates of Formula VI, wherein $Cy^1$ is aryl or heteroaryl substituted with electron withdrawing groups such as $NO_2$ or $CF_3$ and $Z^3$ is fluorine, chlorine or bromine, can be prepared by reaction of hydrazines of Formula XXVII with halides of Formula XXVIII.

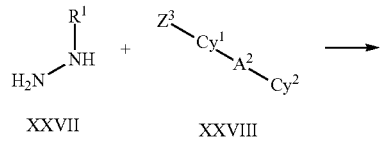

XXVII  XXVIII

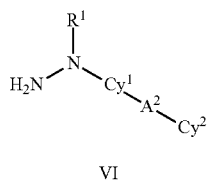

VI

Intermediates of Formula II, wherein n is 0, can be prepared directly by treatment of halide or sulfonate intermediates of Formula XXIX, wherein $Z^4$ is a halide, for example chloride, or sulfonate leaving group $OSO_2R^c$, wherein $R^c$ is alkyl, aryl or haloalkyl, for example p-toluenesulfonyloxy or methylsulfonyloxy, with a hydrazine of Formula VI.

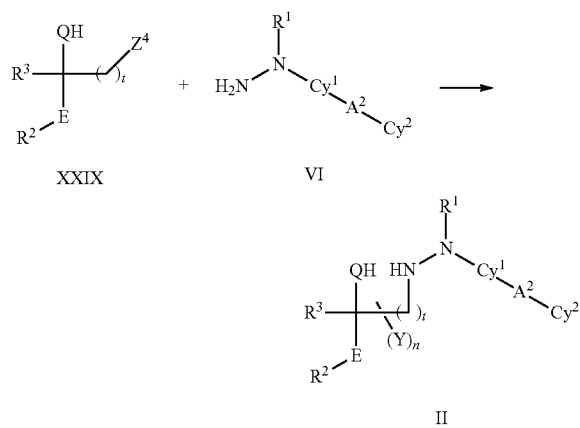

XXIX  VI

II

Intermediates of Formula XXIX, wherein $Z^4$ is a sulfonate can be prepared by reaction of diols of Formula XIX or (preferably N-protected) aminoalcohols of Formula XXX with $R^cSO_2Cl$ or $(R^cSO_2)_2O$.

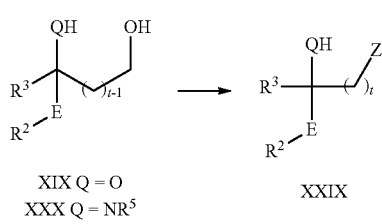

XIX Q = O
XXX Q = $NR^5$
XXIX

Aminoalcohols of Formula XXX, wherein Q is $NR^5$ and t is 2, can be prepared by hydroboration of homoallyl amines of Formula XIV.

Intermediates of Formula XXIX, wherein $Z^4$ is chloride and t is 2, can be prepared by reaction of ketones of Formula XXXI with organometallics of Formula XXXII, wherein M is MgCl, MgBr, MgI or Li. In one embodiment the reaction is carried out in the presence of $CeCl_3$.

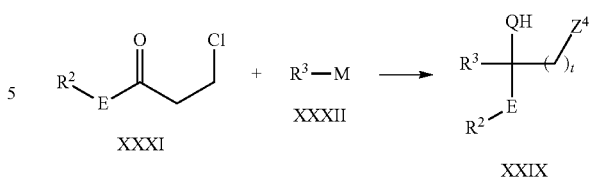

XXXI  XXXII  XXIX

In a second process, a compound of Formula I, wherein $Cy^1$ is cycloalkyl or heterocyclyl and $R^1$ is hydrogen, is prepared by reduction of a hydrazone of Formula XXXIII using, for example, hydrogen in the presence of a palladium or platinum catalyst or a hydride reagent such as $LiAlH_4$, $NaCNBH_3$ or $Bu_3SnH$.

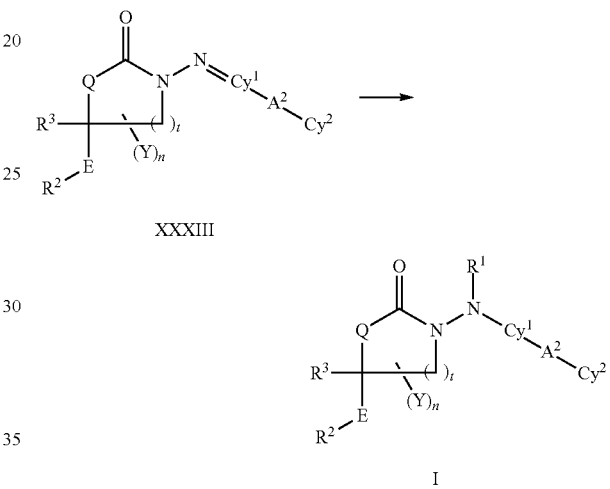

XXXIII

I

Hydrazones of Formula XXXIII can be prepared from hydrazines of Formula XXXIV and ketones of Formula XXXV.

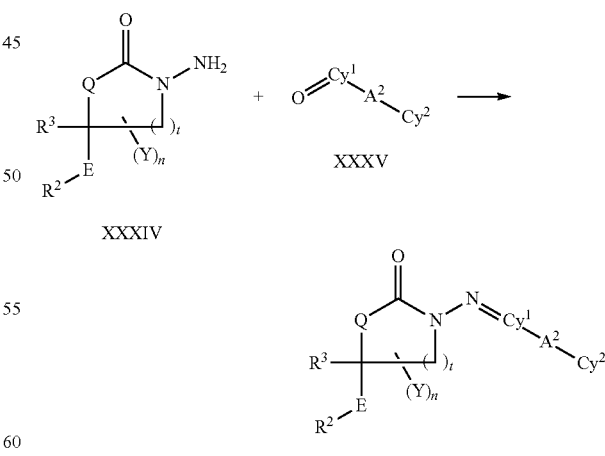

XXXIV  XXXV

XXXIII

Hydrazines of Formula XXXIV can be prepared from cyclic intermediates of Formula XXXVI by nitrosation with, for example, $NaNO_2$ in the presence of acid, followed by reduction.

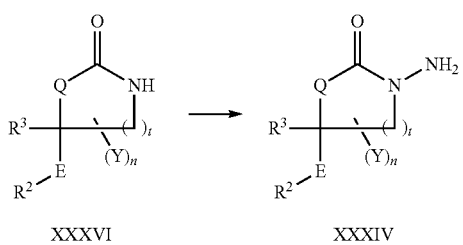

Compounds of Formula XXXVI can be prepared by reaction of aminoalcohols (Q=O) and diamines (Q=NR5) of Formula XXXVII with reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.

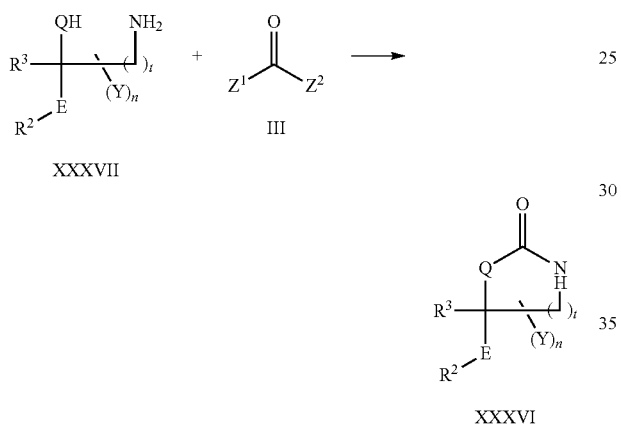

Aminoalcohols (Q=O) and diamines (Q=NR$^5$) of Formula XXXVII, wherein n=0, can be prepared by reaction of halide or sulfonate intermediates of Formula XXIX with ammonia or with sodium azide followed by reduction by catalytic hydrogenation or with $Ph_3P$ in wet THF.

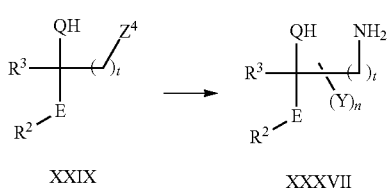

Additional methods for the synthesis of 1,2-diamine intermediates, including those of Formula XXXVII wherein t=1 and Q=NR$^5$, are described in Lucet, D.; Le Gall, T.; Mioskowski, C. *Angew. Chem. Int. Ed.* 1998, 37, 2580-2617.

In a third process, compounds of Formula I wherein n is 0, Q is 0 or NR$^5$, R$^5$ is $(C_1-C_6)$alkyl and R$^1$ is not hydrogen, can be prepared by treatment of compounds of Formula XXIX with isocyanates of Formula XXXVIII, wherein R$^1$ is not H, followed by strong bases such as NaH or DBU, in inert solvents, such as DMF.

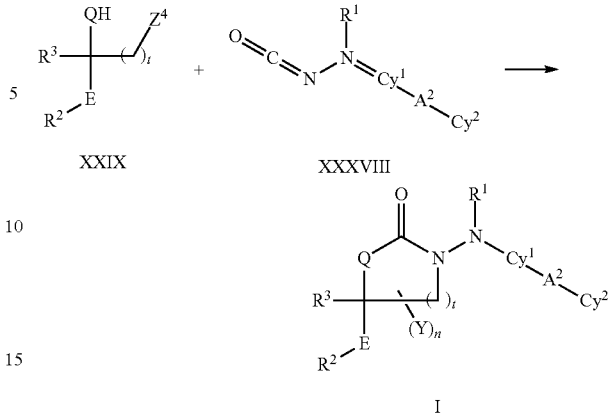

Isocyanates of Formula XXXVIII, wherein R$^1$ is not H, can be prepared by treatment of hydrazines of Formula VI with reagents of Formula III, wherein $Z^1$ and $Z^2$ are leaving groups such as chloride, 1-imidazolyl or aryloxide.

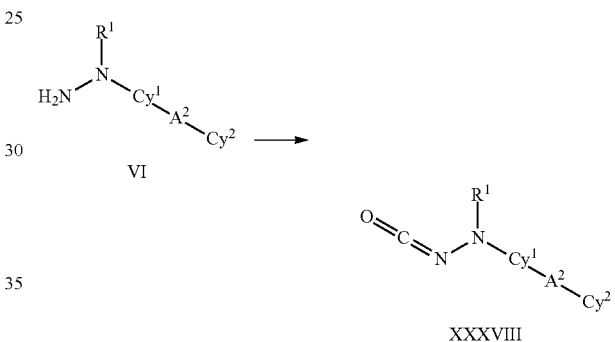

In a fourth process, compounds of Formula I, wherein Cy$^1$ is aryl or heteroaryl, can be prepared by reaction of compounds of Formula XXXIX with halides of Formula XL, wherein $Z^5$ is bromide or iodide, in the presence of a copper or palladium catalyst.

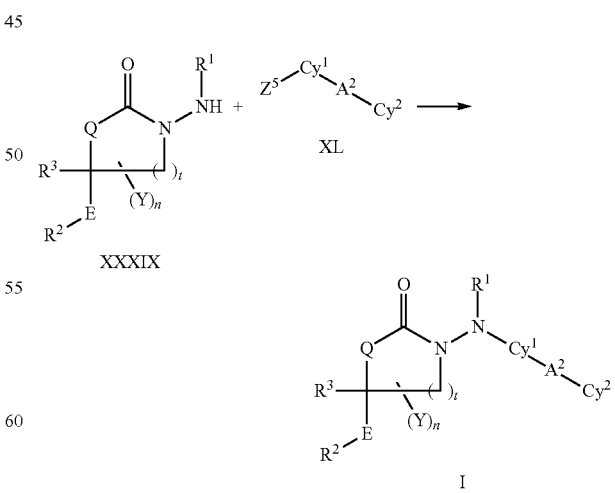

Compounds of Formula XXXIX, wherein R$^1$ is $(C_2-C_6)$ alkyl can be prepared by reduction of hydazones of Formula XLI, wherein R$^{1a}$ is $(C_1-C_5)$alkyl using, for example, hydrogen in the presence of a palladium or platinum catalyst or a hydride reagent such as LiAlH$_4$, NaCNBH$_3$ or Bu$_3$SnH.

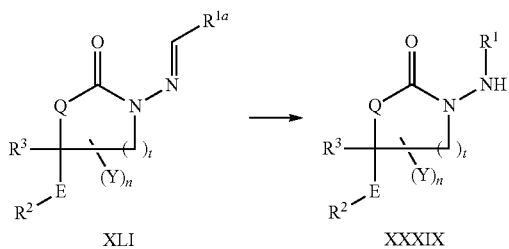

Compounds of Formula XLI, wherein R$^{1a}$ is a straight chain (C$_1$-C$_5$)alkyl can be prepared by reaction of an intermediate of Formula XXXIV with an aldehyde of Formula XLII.

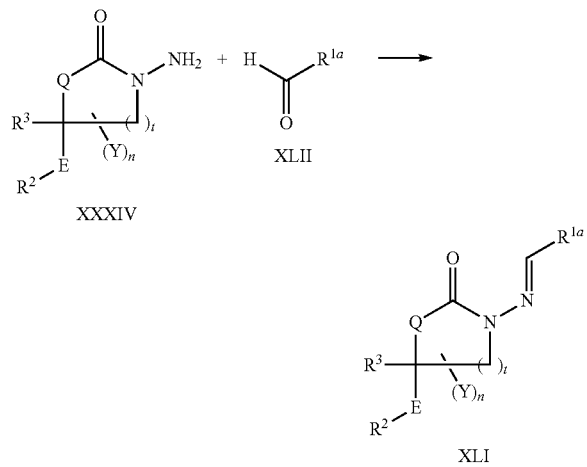

In a fifth process, compounds of Formula I can be prepared from other compounds of Formula I. For example:

(1) a compound of Formula I wherein Cy$^1$ is substituted with bromine or iodine, A$^2$ is a bond and Cy$^2$ is hydrogen can be reacted with an optionally substituted aryl or heteroarylboronic acid or ester in the presence of a palladium catalyst to give a compound of Formula I wherein A$^2$ is a bond and Cy$^2$ is optionally substituted aryl or heteroaryl.

(2) a compound of Formula I wherein R$^1$ or R$^3$ is ω-hydroxy(C$_2$-C$_6$)alkyl can be oxidized to a compound of Formula I wherein R$^1$ or R$^3$ is ω-carboxy(C$_1$-C$_6$)alkyl using Jones reagent.

(3) a compound of Formula I wherein R$^1$ or R$^3$ is ω-carboxy(C$_1$-C$_6$)alkyl can be coupled with ammonia or a (C$_1$-C$_6$)alkylamine using a standard peptide coupling reagent such as EDC to afford a compound of Formula I wherein R$^1$ or R$^3$ is ω-H$_2$NC(=O)(C$_1$-C$_6$)alkyl or ω-{(C$_1$-C$_6$)alkylNHC(=O)}(C$_1$-C$_6$)alkyl.

(4) a compound of Formula I wherein R$^1$ or R$^3$ is ω-hydroxy(C$_1$-C$_6$)alkyl can be converted to its methanesulfonate or trifluoromethanesulfonate, treated with sodium azide and reduced to give a compound of Formula I, wherein R$^1$ or R$^3$ is ω-amino(C$_1$-C$_6$)alkyl.

(5) a compound of Formula I wherein R$^1$ or R$^3$ is amino (C$_1$-C$_6$)alkyl can be reacted with acetic anhydride or acetyl chloride to give a compound of Formula I wherein R$^1$ or R$^3$ is {acetylamino}(C$_1$-C$_6$)alkyl.

(6) a compound of Formula I wherein R$^1$ or R$^3$ is amino (C$_1$-C$_6$)alkyl can be reacted with methanesulfonyl chloride to give a compound of Formula I wherein R$^1$ or R$^3$ is {methanesulfonylamino}(C$_1$-C$_6$)alkyl.

(7) a compound of Formula I, wherein R$^1$ or R$^3$ is (C$_2$-C$_6$)alkenyl is hydroborated to afford a compound of Formula I wherein R$^1$ or R$^3$ is hydroxy(C$_2$-C$_6$)alkyl. When the alkene is at the terminus of the (C$_2$-C$_6$)alkenyl group, the major product is generally the primary ω-hydroxy(C$_2$-C$_6$)alkenyl i and the minor product is the secondary alcohol ii.

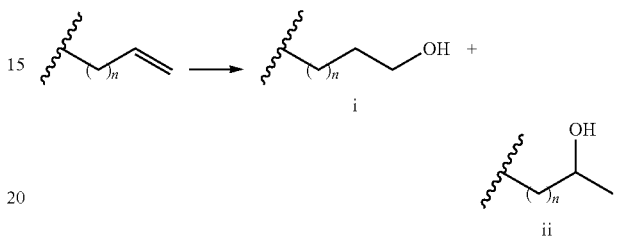

n = 0-4

(8) a compound of Formula I, wherein R$^1$ is (C$_2$-C$_6$)alkenyl, can be reacted with osmium tetroxide and N-methylmorpholine-N-oxide to afford a compound of Formula I wherein R$^1$ is vicinal dihydroxy(C$_2$-C$_6$)alkyl.

(9) a compound of Formula I, wherein R$^3$ is (C$_2$-C$_6$)alkenyl, can be reacted with osmium tetroxide and N-methylmorpholine-N-oxide to afford a vicinal diol compound of Formula I wherein R$^3$ is vicinal dihydroxy(C$_2$-C$_6$)alkyl.

(10) a compound of Formula I, wherein R$^1$ is H$_2$C=CH (C$_0$-C$_4$)alkyl-, can be reacted with ozone followed by NaBH$_4$ to give a compound of Formula I wherein R$^1$ is ω-hydroxy (C$_1$-C$_5$)alkyl.

(11) a compound of Formula I, wherein R$^3$ is H$_2$C=CH (C$_0$-C$_4$)alkyl-, can be reacted with ozone followed by NaBH$_4$ to give a compound of Formula I wherein R$^3$ is ω-hydroxy (C$_1$-C$_5$)alkyl.

(12) a compound of Formula I wherein R$^1$ or R$^3$ is amino (C$_1$-C$_6$)alkyl can be reacted with an (C$_1$-C$_6$)alkyl isocyanate to give a compound of Formula I wherein R$^1$ or R$^3$ is (C$_1$-C$_6$) alkylaminocarbonylamino(C$_1$-C$_6$)alkyl.

(13) a compound of Formula I wherein R$^1$ or R$^3$ is amino (C$_1$-C$_6$)alkyl can be reacted with an (C$_1$-C$_6$)alkyl chloroformate to give a compound of Formula I wherein R$^1$ or R$^3$ is (C$_1$-C$_6$)alkoxycarbonylamino(C$_1$-C$_6$)alkyl.

(14) a compound of Formula I wherein R$^1$ or R$^3$ is amino (C$_1$-C$_6$)alkyl can be reacted with chlorosulfonyl isocyanate or sulfamide to give a compound of Formula I wherein R$^1$ or R$^3$ is aminosulfonylamino(C$_1$-C$_6$)alkyl.

(15) a compound of Formula I wherein R$^1$ or R$^3$ is amino (C$_1$-C$_6$)alkyl can be reacted with a (C$_1$-C$_6$)alkylsulfamoyl chloride to give a compound of Formula I wherein R$^1$ or R$^3$ is (C$_1$-C$_6$)alkylaminosulfonylamino(C$_1$-C$_6$)alkyl.

(16) a compound of Formula I wherein R$^1$ or R$^3$ is hydroxy (C$_1$-C$_6$)alkyl can be reacted with chlorosulfonyl isocyanate to give a compound of Formula I wherein R$^1$ or R$^3$ is aminosulfonyloxy(C$_1$-C$_6$)alkyl.

(17) a compound of Formula I wherein R$^1$ or R$^3$ is hydroxy (C$_1$-C$_6$)alkyl can be reacted with p-nitrophenyl chloroformate, pentafluorophenyl chloroformate or carbonyl diimidazole, followed by ammonia, a (C$_1$-C$_6$)alkylamine or a di(C$_1$-C$_6$)alkylamine to give a compound of Formula I wherein R$^1$ or R³ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$)alkyl.

(18) a compound of Formula I wherein R¹ or R³ is hydroxy ($C_1$-$C_6$)alkyl can be reacted with $POCl_3$ to give a compound of Formula I wherein R¹ or R³ is $(HO)_2P(=O)O(C_1$-$C_6)$alkyl.

(19) a compound of Formula I wherein Cy¹ is substituted with bromine or iodine, A² is a bond and Cy² is hydrogen can be reacted with a cyclic amine in the presence of a palladium catalyst to give a compound of Formula I wherein A² is a bond and Cy² is a cyclic amino moiety attached through its nitrogen atom.

(20) a compound of Formula I wherein Q is NR⁵ and R⁵ is H can be reacted with an ($C_1$-$C_6$)alkyl halide in the presence of a strong base such as sodium hydride to afford a compound of Formula I wherein Q is NR⁵ and R⁵ is ($C_1$-$C_6$)alkyl.

(21) a compound of Formula I wherein R¹ or R³ is ω-$H_2$NCO($C_1$-$C_6$)alkyl can be reacted with TFAA in the presence of pyridine to afford a compound of Formula I wherein R¹ or R³ is ω-cyano($C_1$-$C_6$)alkyl.

(22) a compound of Formula I, wherein R¹ or R³ is ω-$MeO_2$C($C_1$-$C_6$)alkyl can be reacted with at least 2 equivalents of MeMgBr to afford a compound of Formula I, wherein R¹ or R³ is $HOC(Me)_2$($C_1$-$C_6$)alkyl.

(23) a compound of Formula I wherein R¹ or R³ is ω-hydroxy($C_1$-$C_6$)alkyl can be converted to its methanesulfonate or trifluoromethanesulfonate and reacted with morpholine to give a compound of Formula I, wherein R¹ or R³ is ω-(4-morpholino)($C_1$-$C_6$)alkyl.

(24) a compound of Formula I, wherein R¹ is hydrogen, can be treated with NaH and MeI in a solvent such as DMF or THF to afford a compound of Formula I, wherein R¹ is methyl.

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 [LC-MS (3 min)]

Column: Chromolith SpeedRod, RP-18e, 50×4.6 mm; Mobil phase: A: 0.01% TFA/water, B: 0.01% TFA/$CH_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

Example 1

6-allyl-6-(4-fluorophenyl)-3-(methyl(phenyl)amino)-1,3-oxazinan-2-one

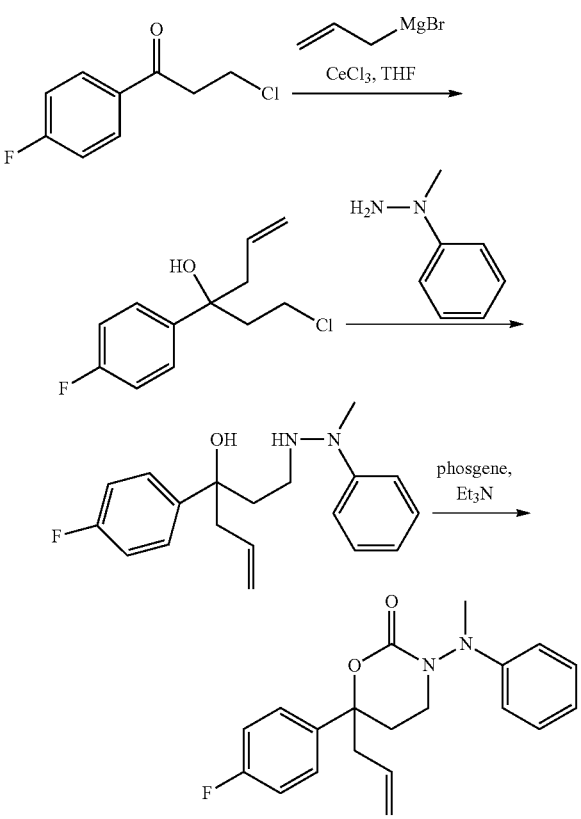

Step 1

A 250-mL flask was charged with anhydrous $CeCl_3$ (5.58 g, 22.6 mmol) and THF (40 mL). The mixture was vigorously stirred for 3.5 h at rt. The suspension was then cooled to −78° C. and a solution of allylmagnesium bromide (1.0 M in THF, 21 mL, 21.0 mmol) was added. After stirring for 2 h at −78° C., a solution of 3-chloro-1-(4-fluorophenyl)propan-1-one (2.522 g, 13.5 mmol) in THF (30 mL) was added via cannula. The reaction mixture was allowed to slowly warm to 8° C. while stirring overnight (18 h). The reaction was then quenched with satd aq $NaHCO_3$, extracted with EtOAc, and dried over $Na_2SO_4$. After the solvents were evaporated, the residue was purified by chromatography on silica gel eluted with hexanes/EtOAc to afford 1-chloro-3-(4-fluorophenyl)hex-5-en-3-ol (3.0049 g, 97%) as an oil. LC-MS Method 1 $t_R$=1.79 min, m/z 213, 211 (M-OH)⁺; ¹H NMR (400 MHz, $CDCl_3$) δ 7.37-7.32 (m, 2H), 7.07-7.02 (m, 2H), 5.57-5.47 (m, 1H), 5.20-5.19 (m, 1H), 5.16 (m, 1H), 3.59-3.52 (m, 1H), 3.24-3.18 (m, 1H), 2.70 (dd, J=13.8, 5.9 Hz, 1H), 2.50 (dd, J=13.8, 8.5 Hz, 1H), 2.29 (t, J=7.9 Hz, 2H), 2.22 (s, 1H); ¹⁹F NMR (376 MHz, $CDCl_3$) δ-116.52 (m).

Step 2

1-chloro-3-(4-fluorophenyl)hex-5-en-3-ol (20 mg, 0.088 mmol) and 1-methyl-1-phenylhydrazine (640 mg, 5.26 mmol) were combined and heated in a microwave for 10 min at 120° C. and for 20 min at 140° C. The crude mixture was purified by chromatography on a silica gel cartridge eluted with an EtOAc/hexanes gradient followed by preparative HPLC to afford 3-(4-fluorophenyl)-1-(2-methyl-2-phenylhydrazinyl)hex-5-en-3-ol (2 mg). LC-MS Method 1 m/z=315 (M+1).

Step 3

3-(4-fluorophenyl)-1-(2-methyl-2-phenylhydrazinyl)hex-5-en-3-ol (14 mg, 0.04 mmol) and triethylamine (3 drops) was dissolved in toluene (1 mL). The solution was cooled to 0° C. and phosgene (3 drops, 20% toluene solution) was added. After 1 h, more phosgene was added (3 drops, 20% toluene solution) and the reaction was allowed to warm to rt overnight. The solvent was evaporated and the residue was redissolved in toluene. DBU (5 drops) was added and the solution heated to reflux for 4 h. The solvent was evaporated and the residue was purified by preparative HPLC to afford 6-allyl-6-(4-fluorophenyl)-3-(methyl(phenyl)amino)-1,3-oxazinan-2-one (8.8 mg). LC-MS Method 1 m/z=341 (M+1). $^1$H NMR (CDCl$_3$) δ 7.43-7.37 (br m), 7.25-7.26 (m), 7.19-7.12 (m), 6.99 (t), 6.85 (m), 6.72-6.66 (m), 6.07 (d), 6.73 (m), 5.15-5.05 (m), 3.42 (m), 3.33 (m), 3.14 (s), 2.85 (s), 2.65-2.55 (m), 2.50-2.34 (m).

Alternative Procedures for Step 2:

(1) 1-chloro-3-(4-fluorophenyl)hex-5-en-3-ol (50 mg, 0.22 mmol) and 1-methyl-1-phenylhydrazine (60 mg, 0.49 mmol) were combined and heated in a microwave for 20 min at 140° C. Starting material was still evident by LC-MS and additional 1-methyl-1-phenylhydrazine (640 mg, 5.26 mmol) was added. The mixture was further heated in a microwave for 20 min at 140° C. The crude mixture was purified by chromatography on a silica gel cartridge eluted with an EtOAc/hexanes gradient and further purified by preparative HPLC to provide 3-(4-fluorophenyl)-1-(2-methyl-2-phenylhydrazinyl)hex-5-en-3-ol (6 mg). LC-MS Method 1 m/z=315 (M+1).

(2) 1-chloro-3-(4-fluorophenyl)hex-5-en-3-ol (58 mg, 0.25 mmol), 1-methyl-1-phenylhydrazine (500 mg, 4.09 mmol), and tetrabutylammonium iodide (92 mg, 0.25 mmol) were combined and heated in a microwave for 50 min at 63° C. The crude mixture was filtered and purified twice by chromatography on a silica gel cartridge eluted with an EtOAc/hexanes gradient to remove 1-methyl-1-phenylhydrazine. The residue was dissolved in Et$_2$O and washed with 1 M aq HCl. The aqueous layer was treated with 1 M aq NaOH until a pH of 4 was reached, then extracted with Et$_2$O. The organic layer was evaporated and the residue was further purified by preparative HPLC to provide 3-(4-fluorophenyl)-1-(2-methyl-2-phenylhydrazinyl)hex-5-en-3-ol (6 mg). LC-MS Method 1 m/z=315 (M+1).

Example 2

6-(4-fluorophenyl)-6-(3-hydroxypropyl)-3-(methyl(phenyl)amino)-1,3-oxazinan-2-one

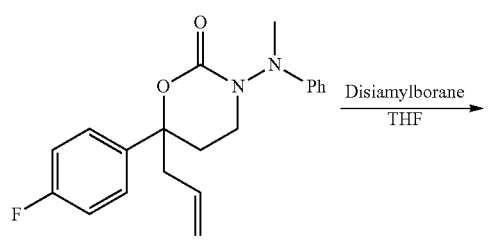

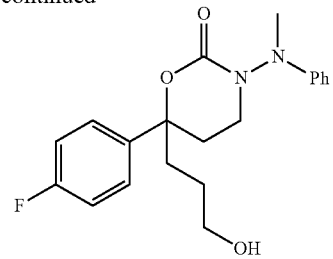

At 0° C., 2M 2-methyl-2-butene in THF (15 mL, 30 mmol) was added to BH$_3$.DMS (1.5 mL, 15 mmol, 10M) in THF (3 mL) and stirred for 1 h to afford a 0.83 M THF solution of disiamylborane. In a separate flask, disiamylborane (0.1 mL, 0.08 mmol) was added to 6-allyl-6-(4-fluorophenyl)-3-(methyl(phenyl)amino)-1,3-oxazinan-2-one (6 mg, 0.018 mmol) in THF (1 mL) at 0° C. The reaction was warmed to rt overnight. The reaction was cooled to 0° C. and quenched with H$_2$O (1 mL) and stirred for 15 min at rt. NaBO$_3$ (22 mg, 0.22 mmol) was added and the reaction was stirred for 2 h. The solvent was evaporated and the crude material purified by prep HPLC to afford 6-(4-fluorophenyl)-6-(3-hydroxypropyl)-3-(methyl(phenyl)amino)-1,3-oxazinan-2-one (1.16 mg). LC/MS Method 1 t$_R$=1.51 min m/z=359 (M+1).

Biological Test Example 1

The inhibition of microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxysteroid Dehydrogenase Type 1 in Scintillation Proximity Assay Format. Assay Drug Dev Technol 3 (2005) 377-384). All reactions were carried out at room temperature in 96 well clear flexible PET Microbeta plates (PerkinElmer). The assay begins by dispensing 49 µl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 µL of the test compounds in DMSO previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) was added, and the plates were incubated for 90 minutes at room temperature. The reaction was stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superblock buffer (Bio-Rad). The plates were shaken for 120 minutes at room temperature, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 µL. The cells were pre-incubated with serum-free, phenol-red-free medium containing 0.1% (v/v) of DMSO and various concentrations of the test compounds at least 1 h before [$^3$H] cortisone in ethanol (50Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 µL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

| TABLE OF BIOLOGICAL ASSAY RESULTS | | |
|---|---|---|
| | Biological Test Example 1 | |
| Compound | IC$_{50}$ Range[a] | % Inhibition at 100 nM |
| Example 1 | ++ | 55.4 |
| Example 2 | # | 36.8 |

[a] ++ means IC$_{50}$ = <100 nM, + means IC$_{50}$ = 100-1000 nM, # means IC$_{50}$ >100 nM, nt means not tested.

Prophetic Compound Tables

TABLE 1

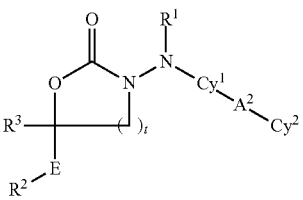

I* t = 1, 2 or 3

| Cpd. No. | R$^1$ | Cy$^1$ [a] | A$^2$ | Cy$^2$ | E | R$^2$ | R$^3$ |
|---|---|---|---|---|---|---|---|
| 1a | Me | 1,4-C$_6$H$_4$ | bond | 2,4-diF—Ph | bond | 4-F—Ph | H$_2$NC(=O)CH$_2$ |
| 2a | Me | 1,4-C$_6$H$_4$ | bond | 2,4-diF—Ph | bond | 4-F—Ph | HOCH$_2$CH(OH)CH$_2$ |
| 3a | Me | Ph | bond | H | bond | Ph | Me |
| 4a | Me | 3-MeO—Ph | bond | H | bond | Ph | Me |
| 5a | Me | 4-MeO—Ph | bond | H | bond | Ph | Me |
| 6a | Me | Ph | bond | H | bond | 2-Me—Ph | Me |
| 7a | Me | Ph | bond | H | bond | 4-Me—Ph | Me |
| 8a | Me | Ph | bond | H | bond | 4-MeS—Ph | Me |
| 9a | Me | Ph | bond | H | bond | 2-F—Ph | allyl |
| 10a | Me | Ph | bond | H | bond | 4-F—Ph | HOCH$_2$CH$_2$ |
| 11a | Me | 4-Br—Ph | bond | H | bond | 4-F—Ph | allyl |
| 12a | Me | 1,4-C$_6$H$_4$ | bond | 2,4-diF—Ph | bond | 4-F—Ph | allyl |
| 13a | Me | 1,4-C$_6$H$_4$ | bond | 2,4-diF—Ph | bond | 4-F—Ph | HOCH$_2$CH$_2$ |
| 14a | Me | Ph | bond | H | bond | 4-F—Ph | vinyl |
| 15a | Me | 4-Br—Ph | bond | H | bond | 4-F—Ph | HOCH$_2$CH$_2$ |
| 16a | Me | 1,4-C$_6$H$_4$ | bond | 4-F—Ph | bond | 4-F—Ph | HOCH$_2$CH$_2$ |
| 17a | Me | c-hex | bond | H | bond | 4-F—Ph | allyl |
| 18a | Me | c-hex | bond | H | bond | 4-F—Ph | HOCH$_2$CH$_2$CH$_2$ |
| 19a | Me | 1,4-C$_6$H$_4$ | bond | c-Pr | bond | 4-F—Ph | allyl |
| 20a | Me | 4-MeO$_2$C—Ph | bond | H | bond | 4-F—Ph | allyl |
| 21a | Me | 1,4-C$_6$H$_4$ | bond | c-Pr | bond | 4-F—Ph | HOCH$_2$CH$_2$CH$_2$ |
| 22a | Me | 4-MeO2C—Ph | bond | H | bond | 4-F—Ph | HOCH$_2$CH$_2$CH$_2$ |
| 23a | Et | 4-Br—Ph | bond | H | bond | 4-F—Ph | allyl |
| 24a | Me | 1,4-C$_6$H$_4$ | bond | 2,4-diF—Ph | bond | 4-F—Ph | H$_2$NCH$_2$CH$_2$ |
| 25a | Me | 1,4-C$_6$H$_4$ | bond | 2,4-diF—Ph | bond | 4-F—Ph | HOCH$_2$CH$_2$CH$_2$ |
| 26a | Me | 1,4-C$_6$H$_4$ | bond | 2,4-diF—Ph | bond | 4-F—Ph | MeCH(OH)CH$_2$ |
| 27a | Me | 1,4-C$_6$H$_4$ | bond | 2,4-diF—Ph | bond | 4-F—Ph | MeC(=O)CH$_2$ |
| 28a | Me | 1,4-C$_6$H$_4$ | bond | 2,4-diF—Ph | bond | 4-F—Ph | HOC(Me)$_2$CH$_2$ |
| 29a | Me | 1,4-C$_6$H$_4$ | bond | 2,4-diF—Ph | bond | 4-F—Ph | MeOCH$_2$CH$_2$ |
| 30a | Me | 1,4-C$_6$H$_4$ | bond | 2,4-diF—Ph | bond | 4-F—Ph | MeNHC(=O)NHCH$_2$CH$_2$ |
| 31a | Me | 4-Br—Ph | bond | H | bond | 4-F—Ph | HOCH$_2$CH$_2$ |
| 32a | Me | 4-Br—Ph | bond | H | bond | 4-F—Ph | HOCH$_2$CH(OH)CH$_2$ |
| 33a | Me | 1,4-C$_6$H$_4$ | bond | 2,4-diF—Ph | bond | 4-F—Ph | H$_2$NCOCH$_2$CH$_2$ |

TABLE 1-continued

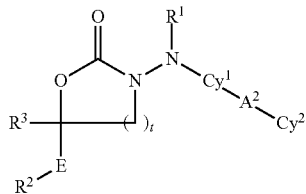

t = 1, 2 or 3

| Cpd. No. | R¹ | Cy¹ᵃ | A² | Cy² | E | R² | R³ |
|---|---|---|---|---|---|---|---|
| 34a | Me | 1,4-C$_6$H$_4$ | bond | 2,4-diF—Ph | bond | 4-F—Ph | MeNHC(=O)CH$_2$CH$_2$ |
| 35a | Me | 1,4-C$_6$H$_4$ | bond | 2,4-diF—Ph | bond | 4-F—Ph | MeCONHCH$_2$CH$_2$ |
| 36a | Me | 1,4-C$_6$H$_4$ | bond | 2,4-diF—Ph | bond | 4-F—Ph | MeNHC(=O)OCH$_2$CH$_2$ |
| 37a | Me | 1,4-C$_6$H$_4$ | bond | 2,4-diF—Ph | bond | 4-F—Ph | H$_2$NSO$_2$NHCH$_2$CH$_2$ |
| 38a | Me | 1,4-C$_6$H$_4$ | bond | 2,4-diF—Ph | bond | 4-F—Ph | H$_2$NSO$_2$OCH$_2$CH$_2$ |
| 39a | Me | 1,4-C$_6$H$_4$ | bond | 2,4-diF—Ph | bond | 4-F—Ph | (HO)$_2$P(=O)OCH$_2$CH$_2$ |
| 40a | Me | 1,4-C$_6$H$_4$ | bond | 2,4-diF—Ph | bond | 4-F—Ph | H$_2$NCH$_2$C(=O)NHCH$_2$CH$_2$ |
| 41a | Me | 4-HOCH$_2$—Ph | bond | H | bond | 4-F—Ph | HOCH$_2$CH$_2$CH$_2$ |
| 42a | Me | 4-HOC(Me)$_2$—Ph | bond | H | bond | 4-F—Ph | allyl |
| 43a | Me | 4-Br—Ph | bond | H | bond | 2-thienyl | allyl |
| 44a | Me | 1,4-C$_6$H$_4$ | bond | 4-F—Ph | bond | Ph | HOCH$_2$CH$_2$ |
| 45a | Me | 1,4-C$_6$H$_4$ | bond | 4-F—Ph | bond | 2-thienyl | allyl |
| 46a | Me | 1,4-C$_6$H$_4$ | bond | 4-F—Ph | bond | Ph | HOCH$_2$CH$_2$CH$_2$ |
| 47a | Me | 1,4-C$_6$H$_4$ | bond | 2,4-diF—Ph | bond | Ph | HOCH$_2$CH$_2$ |
| 48a | Me | 1,4-C$_6$H$_4$ | bond | 2,4-diF—Ph | bond | 2-thienyl | allyl |
| 49a | Me | 1,4-C$_6$H$_4$ | bond | 4-F—Ph | bond | 2-thienyl | HOCH$_2$CH$_2$CH$_2$ |
| 50a | Me | 1,4-C$_6$H$_4$ | bond | 4-F—Ph | bond | 2-thienyl | MeCH(OH)CH$_2$ |
| 51a | Me | 1,4-C$_6$H$_4$ | bond | 4-F—Ph | bond | Ph | HOCH$_2$CH(OH)CH$_2$ |
| 52a | Me | 1,4-C$_6$H$_4$ | bond | 2,4-diF—Ph | bond | Ph | HOCH$_2$CH$_2$CH$_2$ |
| 53a | Me | 1,4-C$_6$H$_4$ | bond | 2,4-diF—Ph | bond | Ph | MeCH(OH)CH2 |
| 54a | Me | 1,4-C$_6$H$_4$ | bond | 2,4-diF—Ph | bond | 2-thienyl | HOCH$_2$CH$_2$CH$_2$ |
| 55a | Me | 1,4-C$_6$H$_4$ | bond | 2,4-diF—Ph | bond | 4-F—Ph | NCCH$_2$CH$_2$ |
| 56a | Me | 1,4-C$_6$H$_4$ | bond | 2,4-diF—Ph | bond | Ph | HOCH$_2$CH(OH)CH$_2$ |
| 57a | Et | 1,4-C$_6$H$_4$ | bond | 2,4-diF—Ph | bond | 4-F—Ph | HOCH$_2$CH$_2$ |
| 58a | Me | 1,4-C$_6$H$_4$ | bond | 2,4-diF—Ph | bond | 4-F—Ph | HOC(=O)CH$_2$CH$_2$ |
| 59a | Me | 1,4-C$_6$H$_4$ | bond | 2,4-diF—Ph | bond | 4-F—Ph | HOCH$_2$CH$_2$NHCH$_2$CH$_2$ |
| 60a | Me | 1,4-C$_6$H$_4$ | bond | 2,4-diF—Ph | bond | 4-F—Ph | HOCH$_2$C(=O)NHCH$_2$CH$_2$ |
| 61a | Me | 1,4-C$_6$H$_4$ | bond | 2,4-diF—Ph | bond | 4-F—Ph | MeOC(=O)NHCH$_2$CH$_2$ |
| 62a | Me | 1,4-C$_6$H$_4$ | bond | 2,4-diF—Ph | bond | 4-F—Ph | 2-(4-morpholino)ethyl |
| 63a | Me | 1,4-C$_6$H$_4$ | bond | 2,4-diF—Ph | bond | 4-F—Ph | EtNHCONHCH$_2$CH$_2$ |
| 64a | Me | 1,4-C$_6$H$_4$ | bond | 2,4-diF—Ph | bond | 4-F—Ph | MeNHC(=NCN)NHCH$_2$CH$_2$ |
| 65a | Me | 1,4-C$_6$H$_4$ | bond | 2,4-diF—Ph | bond | 4-F—Ph | MeSO2NHCH$_2$CH$_2$CH$_2$ |
| 66a | Me | 4-Cl—Ph | bond | H | bond | i-Pr | HOCH$_2$CH$_2$CH$_2$ |
| 67a | Me | 4-Me—Ph | bond | H | bond | 4-F—Ph | allyl |
| 68a | Me | 4-MeO—Ph | bond | H | bond | Ph | HOCH$_2$CH$_2$ |
| 69a | Me | 4-MeO—Ph | bond | H | bond | Ph | allyl |
| 70a | Me | 4-HOCH$_2$—Ph | bond | H | bond | Ph | HOCH$_2$CH$_2$CH$_2$ |
| 71a | Me | 4-MeO—Ph | bond | H | bond | 4-F—Ph | HOCH$_2$CH$_2$ |
| 72a | Me | 4-Cl—Ph | bond | H | bond | 4-F—Ph | allyl |
| 73a | Me | c-hex | bond | H | bond | Ph | HOCH$_2$CH(OH)CH$_2$ |
| 74a | Me | 4-HOCH$_2$CH$_2$—Ph | bond | H | bond | Ph | HOCH$_2$CH$_2$CH$_2$ |
| 75a | Me | 4-MeOCH$_2$—Ph | bond | H | bond | Ph | HOCH$_2$CH$_2$CH$_2$ |
| 76a | Me | 4-Br—Ph | bond | H | bond | i-Pr | HOCH$_2$CH$_2$CH$_2$ |
| 77a | Me | 4-Cl—Ph | bond | H | bond | 4-F—Ph | HOCH$_2$CH$_2$CH$_2$ |
| 78a | Me | 4-Cl—Ph | bond | H | bond | 4-F—Ph | MeCH(OH)CH$_2$ |
| 79a | Me | 4-Br—Ph | bond | H | bond | Ph | allyl |
| 80a | Me | 1,4-C$_6$H$_4$ | bond | 3-pyridyl | bond | Ph | HOCH$_2$CH$_2$ |
| 81a | Me | 4-MeO—Ph | bond | H | bond | 4-F—Ph | HOCH$_2$CH(OH)CH$_2$ |
| 82a | Me | 1,4-C$_6$H$_4$ | bond | 2,4-diF—Ph | bond | i-Pr | HOCH2CH2 |
| 83a | Me | 1,4-C$_6$H$_4$ | bond | 2,4-diF—Ph | bond | 4-F—Ph | MeSO$_2$NHCH$_2$CH$_2$ |
| 84a | Me | 1,4-C$_6$H$_4$ | bond | 4-pyridyl | bond | Ph | HOCH$_2$CH$_2$CH$_2$ |
| 85a | Me | 1,4-C$_6$H$_4$ | bond | 3-pyridyl | bond | Ph | HOCH$_2$CH$_2$CH$_2$ |
| 86a | Me | 1,4-C$_6$H$_4$ | bond | 2,4-diF—Ph | bond | i-Pr | HOCH$_2$CH$_2$CH$_2$ |
| 87a | Me | 1,4-C$_6$H$_4$ | bond | 3-pyridyl | bond | 4-F—Ph | HOCH2CH2 |
| 88a | Me | 1,4-C$_6$H$_4$ | bond | 2-thienyl | bond | Ph | HOCH$_2$CH$_2$CH$_2$ |
| 89a | Me | 1,4-C$_6$H$_4$ | bond | 4-morpholinyl | bond | 4-F—Ph | allyl |
| 90a | Me | 1,4-C$_6$H$_4$ | bond | 4-F—Ph | bond | 2-thienyl | HOCH$_2$CH$_2$ |
| 91a | Me | 1,4-C$_6$H$_4$ | bond | 4-F—Ph | bond | Ph | NCCH$_2$CH$_2$ |
| 92a | Et | 4-Br—Ph | bond | H | bond | Ph | HOCH$_2$CH$_2$CH$_2$ |
| 93a | Me | 1,4-C$_6$H$_4$ | bond | 2-oxo-5-(1,2-dihydropyridyl) | bond | Ph | HOCH$_2$CH$_2$CH$_2$ |
| 94a | Me | 1,4-C$_6$H$_4$ | bond | 1-oxo-3-pyridyl | bond | Ph | HOCH$_2$CH$_2$CH$_2$ |
| 95a | Me | 1,4-C$_6$H$_4$ | bond | 2,4-diF—Ph | bond | i-Pr | HOCH$_2$CH(OH)CH$_2$ |

TABLE 1-continued

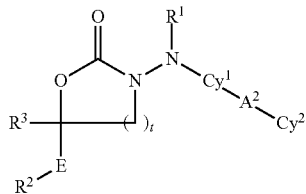

I* t = 1, 2 or 3

| Cpd. No. | R¹ | Cy¹ᵃ | A² | Cy² | E | R² | R³ |
|---|---|---|---|---|---|---|---|
| 96a | Me | 1,4-C₆H₄ | bond | 4-F—Ph | bond | Ph | MeCH(OH)CH₂ |
| 97a | Me | 1,4-C₆H₄ | bond | 3-pyridyl | bond | 4-F—Ph | HOCH2CH2CH2 |
| 98a | Me | 1,4-C₆H₄ | bond | 2,4-diF—Ph | bond | Ph | Pr |
| 99a | Me | 4-Br—Ph | bond | H | bond | 4-F—Ph | HOCH₂CH₂CH₂ |
| 100a | Me | 1,4-C₆H₄ | bond | 2,4-diF—Ph | bond | 4-F—Ph | MeSO₂CH₂CH₂ |
| 101a | Me | 1,4-C₆H₄ | bond | 5-Me-1,3,4-thiadiazol-2-yl | bond | 4-F—Ph | allyl |
| 102a | Me | 1,4-C₆H₄ | bond | 4-F—Ph | bond | 2-thienyl | HOCH₂CH₂CH₂ |
| 103a | Me | 1,4-C₆H₄ | bond | 2,4-diF—Ph | bond | 2-thienyl | HOCH₂CH₂ |
| 104a | Me | 1,4-C₆H₄ | bond | 4-F—Ph | bond | Ph | H₂NCOCH₂CH₂ |
| 105a | Me | 1,4-C₆H₄ | bond | 2-MeO-5-pyridyl | bond | Ph | HOCH₂CH₂CH₂ |
| 106a | Me | 1,4-C₆H₄ | bond | 3-pyridyl | bond | 4-F—Ph | HOCH₂CH₂CH₂ |
| 107a | Et | 1,4-C₆H₄ | bond | 4-F—Ph | bond | Ph | HOCH₂CH₂CH₂ |
| 108a | Me | 1,4-C₆H₄ | bond | 4-F—Ph | bond | Ph | HOC(Me)₂CH₂ |
| 109a | Et | 4-Br—Ph | bond | H | bond | Ph | HOCH₂CH(OH)CH₂ |
| 110a | Me | 4-Br—Ph | bond | H | bond | 4-F—Ph | H₂NCOCH₂CH₂ |
| 111a | Et | 4-Br—Ph | bond | H | bond | 4-F—Ph | HOCH₂CH₂CH₂ |
| 112a | Me | 1,4-C₆H₄ | bond | 2,4-diF—Ph | bond | 4-F—Ph | NCCH₂ |
| 113a | Me | 1,4-C₆H₄ | bond | 2,4-diMe-5-thiazolyl | bond | 4-F—Ph | allyl |
| 114a | Me | 1,4-C₆H₄ | bond | 4-F—Ph | bond | 4-F—Ph | HOCH₂CH₂CH₂ |
| 115a | Me | 1,4-C₆H₄ | bond | 4-F—Ph | bond | 2-F—Ph | HOCH₂CH₂CH₂ |
| 116a | Me | 1,4-C₆H₄ | bond | 4-F—Ph | bond | 3-F—Ph | HOCH₂CH₂CH₂ |
| 117a | Me | 1,4-C₆H₄ | bond | 4-F—Ph | bond | Ph | HOC(Me)₂CH₂CH₂ |
| 118a | Me | 1,4-C₆H₄ | bond | 5-MeCO-2-thienyl | bond | Ph | HOCH₂CH₂CH₂ |
| 119a | Me | 1,4-C₆H₄ | bond | 2,4-diF—Ph | bond | Ph | H₂NCOCH₂CH₂ |
| 120a | Me | 1,4-C₆H₄ | bond | 5-(H₂NCHMe)-2-thienyl | bond | Ph | HOCH₂CH₂CH₂ |
| 121a | Et | 1,4-C₆H₄ | bond | 4-F—Ph | bond | 4-F—Ph | HOCH₂CH₂CH₂ |
| 122a | Et | 1,4-C₆H₄ | bond | 2,4-diF—Ph | bond | Ph | HOCH₂CH₂CH₂ |
| 123a | Me | 1,4-C₆H₄ | bond | 5-(HOCHMe)-2-thienyl | bond | Ph | HOCH₂CH₂CH₂ |
| 124a | Et | 4-Br—Ph | bond | H | bond | 4-F—Ph | HOCH₂CH(OH)CH₂ |
| 125a | Me | 1,4-C₆H₄ | bond | 2,4-diF—Ph | bond | 4-F—Ph | H2NCH₂CH₂CH₂ |
| 126a | Me | 1,4-C₆H₄ | bond | 2,4-diF—Ph | bond | 4-F—Ph | MeNHCH₂CH₂ |
| 127a | Me | 1,4-C₆H₄ | bond | 3-(CF₃)-1-pyrazolyl | bond | 4-F—Ph | allyl |
| 128a | Me | 1,4-C₆H₄ | bond | 2,4-diF—Ph | bond | Ph | HOC(Me)₂CH₂CH₂ |
| 129a | Et | 1,4-C₆H₄ | bond | 2,4-diF—Ph | bond | 4-F—Ph | HOCH₂CH₂CH₂ |
| 130a | Me | 1,4-C₆H₄ | bond | 2,4-diF—Ph | bond | 4-F—Ph | MeSCH₂CH₂ |
| 131a | Me | Ph | bond | 2,4-diF—Ph | bond | 4-F—Ph | H₂NCOCH₂CH₂ |
| 132a | Me | 1,4-C₆H₄ | bond | 2,4-diF—Ph | bond | 4-F—Ph | H₂NCOCH₂CH₂ |
| 133a | Me | 1,4-C₆H₄ | bond | 2,4-diF—Ph | bond | 4-F—Ph | HOCH₂CH₂OCH₂CH₂ |
| 134a | Me | 1,4-C₆H₄ | bond | 2,4-diF—Ph | bond | 4-F—Ph | 2-(1-imidazolyl)ethyl |
| 135a | Me | 1,4-C₆H₄ | bond | 2,4-diF—Ph | bond | 4-F—Ph | MeCONMeCH₂CH₂ |
| 136a | Me | 1,4-C₆H₄ | bond | 4-F—Ph | bond | Ph | MeSO₂NHCH₂CH₂CH₂ |
| 137a | Me | 1,4-C₆H₄ | bond | 2,4-diF—Ph | bond | 4-F—Ph | H₂NC(=O)NHCH₂CH₂CH₂ |
| 138a | Me | 1,4-C₆H₄ | bond | 2,4-diF—Ph | bond | 4-F—Ph | H₂NC(=O)OCH₂CH₂CH₂ |
| 139a | Me | 1,4-C₆H₄ | bond | 2,4-diF—Ph | bond | 4-F—Ph | 2-(1-aminoimidazol-1-yl)ethyl |
| 140a | Me | 1,4-C₆H₄ | bond | 2,4-diF—Ph | bond | 4-F—Ph | MeNHC(=O)NHCH₂CH₂CH₂ |
| 141a | Me | 1,4-C₆H₄ | bond | 2,4-diF—Ph | bond | 4-F—Ph | H₂NC(=O)NHCH₂CH(OH)CH₂ |
| 142a | Me | 1,4-C₆H₄ | bond | 4-F—Ph | bond | 4-F—Ph | MeSO₂NHCH₂CH₂CH₂ |
| 143a | Me | 1,4-C₆H₄ | bond | 4-F—Ph | bond | 4-F—Ph | MeSO₂NMeCH₂CH(OH)CH₂ |
| 144a | Me | 1,4-C₆H₄ | bond | 6-CF₃-3-pyridyl | bond | 4-F—Ph | HOCH₂CH₂CH₂ |
| 145a | Me | 4-MeO—Ph | bond | H | bond | Ph | HOCH₂CH₂CH₂ |
| 146a | Me | 3-F—Ph | bond | H | bond | 4-F—Ph | HOCH₂CH₂CH₂ |
| 147a | Me | 2-F—Ph | bond | H | bond | 4-F—Ph | HOCH₂CH₂CH₂ |
| 148a | Me | 4-F—Ph | bond | H | bond | 4-F—Ph | HOCH₂CH₂CH₂ |
| 149a | Me | 4-MeO—Ph | bond | H | bond | Ph | HOCH₂CH(OH)CH₂ |
| 150a | Me | 4-Cl—Ph | bond | H | bond | Ph | H₂NCOCH₂CH₂ |
| 151a | Me | 4-MeO—Ph | bond | H | bond | 4-F—Ph | H₂NCOCH₂CH₂ |
| 152a | Me | 4-F₂HCO—Ph | bond | H | bond | 4-F—Ph | allyl |
| 153a | Me | Ph | bond | 3-pyrazolyl | bond | Ph | HOCH₂CH₂CH₂ |

TABLE 1-continued

I* structure shown: oxazolidinone with N-R¹, N-Cy¹-A²-Cy², R², R³, E substituents; t = 1, 2 or 3

| Cpd. No. | R¹ | Cy¹ [a] | A² | Cy² | E | R² | R³ |
|---|---|---|---|---|---|---|---|
| 154a | Me | 1,4-C₆H₄ | bond | 5-F-3-pyridyl | bond | Ph | allyl |
| 155a | Me | 3-CF₃—Ph | bond | H | bond | 4-F—Ph | HOCH₂CH₂CH₂ |
| 156a | Me | 4-CF₃—Ph | bond | H | bond | 4-F—Ph | HOCH₂CH₂CH₂ |
| 157a | Me | 1,4-C₆H₄ | bond | 3-pyridyl | bond | Ph | HOCH₂CH₂CH₂ |
| 158a | Me | 1,4-C₆H₄ | bond | 4-pyridyl | bond | Ph | HOCH₂CH₂CH₂ |
| 159a | Me | 1,4-C₆H₄ | bond | 4-F—Ph | bond | Ph | HOCH₂CH₂CH₂ |
| 160a | Me | 1,4-C₆H₄ | bond | 5-F-3-pyridyl | bond | Ph | HOCH₂CH₂CH₂ |
| 161a | Me | 4-MeO—Ph | bond | H | bond | 4-F—Ph | MeSO₂NHCH₂CH₂ |
| 162a | Me | 1,4-C₆H₄ | bond | 5-F-3-pyridyl | bond | 4-F—Ph | HOCH₂CH₂CH₂ |
| 163a | Me | 1,4-C₆H₄ | bond | 4-F—Ph | bond | Ph | NCC(Me)2CH2 |
| 164a | Me | 1,4-C₆H₄ | bond | 6-MeO-3-pyridyl | bond | Ph | H₂NCOCH₂CH₂ |
| 165a | Me | 1,4-C₆H₄ | bond | 5-MeO-3-pyridyl | bond | 4-F—Ph | HOCH₂CH₂CH₂ |
| 166a | Me | 1,4-C₆H₄ | bond | 5-Cl-3-pyridyl | bond | 4-F—Ph | HOCH₂CH₂CH₂ |
| 167a | Me | 1,4-C₆H₄ | bond | 3-pyridyl | bond | Ph | MeSO₂NHCH₂CH₂ |
| 168a | Me | 4-F₂HCO—Ph | bond | H | bond | 4-F—Ph | HOCH₂CH₂CH₂ |
| 169a | Me | 1,4-C₆H₄ | bond | 4-F—Ph | bond | Ph | (HO)₂P(=O)OCH₂CH₂CH₂ |
| 170a | Me | 1,4-C₆H₄ | bond | 2-Me-4-pyridyl | bond | 4-F—Ph | HOCH₂CH₂CH₂ |
| 171a | Me | 4-(HOC(Me)₂CH₂—Ph | bond | H | bond | Ph | HOCH₂CH₂CH₂ |
| 172a | Me | 1,4-C₆H₄ | bond | 1-Me-6-oxo-3-(1,6-dihydropyridyl) | bond | Ph | HOCH₂CH₂CH₂ |
| 173a | Me | 4-MeO—Ph | bond | H | bond | 4-F—Ph | MeSO₂NHCH₂CH₂CH₂ |
| 174a | Me | 4-MeO—Ph | bond | H | bond | Ph | H₂NCOCH₂CH₂ |
| 175a | Me | 4-F—Ph | bond | H | bond | 4-F—Ph | H₂NCOCH₂CH₂ |
| 176a | Me | c-hex | bond | H | bond | 4-F—Ph | H₂NCOCH₂CH₂ |
| 177a | Me | c-hex | bond | H | bond | 4-F—Ph | MeSO₂NHCH₂CH₂ |

[a] Cy¹ = 1,3-C₆H₄ means 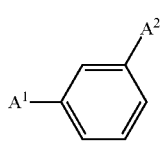

Cy¹ = 1,4-C₆H₄ means 

Cy¹ = 1,3-(4-F)C₆H₃ means 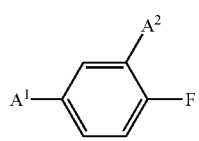

TABLE 2

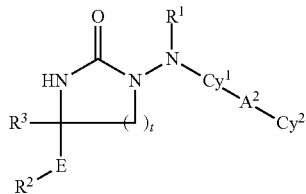

I** t = 1, 2 or 3

| Cpd. No. | R¹ | Cy¹ᵃ | A² | Cy² | E | R² | R³ |
|---|---|---|---|---|---|---|---|
| 1b | Me | 1,4-C₆H₄ | bond | 2,4-diF—Ph | bond | 4-F—Ph | H₂NC(=O)CH₂ |
| 2b | Me | 1,4-C₆H₄ | bond | 2,4-diF—Ph | bond | 4-F—Ph | HOCH₂CH(OH)CH₂ |
| 3b | Me | Ph | bond | H | bond | Ph | Me |
| 4b | Me | 3-MeO—Ph | bond | H | bond | Ph | Me |
| 5b | Me | 4-MeO—Ph | bond | H | bond | Ph | Me |
| 6b | Me | Ph | bond | H | bond | 2-Me—Ph | Me |
| 7b | Me | Ph | bond | H | bond | 4-Me—Ph | Me |
| 8b | Me | Ph | bond | H | bond | 4-MeS—Ph | Me |
| 9b | Me | Ph | bond | H | bond | 2-F—Ph | allyl |
| 10b | Me | Ph | bond | H | bond | 4-F—Ph | HOCH₂CH₂ |
| 11b | Me | 4-Br—Ph | bond | H | bond | 4-F—Ph | allyl |
| 12b | Me | 1,4-C₆H₄ | bond | 2,4-diF—Ph | bond | 4-F—Ph | allyl |
| 13b | Me | 1,4-C₆H₄ | bond | 2,4-diF—Ph | bond | 4-F—Ph | HOCH₂CH₂ |
| 14b | Me | Ph | bond | H | bond | 4-F—Ph | vinyl |
| 15b | Me | 4-Br—Ph | bond | H | bond | 4-F—Ph | HOCH₂CH₂ |
| 16b | Me | 1,4-C₆H₄ | bond | 4-F—Ph | bond | 4-F—Ph | HOCH₂CH₂ |
| 17b | Me | c-hex | bond | H | bond | 4-F—Ph | allyl |
| 18b | Me | c-hex | bond | H | bond | 4-F—Ph | HOCH₂CH₂CH₂ |
| 19b | Me | 1,4-C₆H₄ | bond | c-Pr | bond | 4-F—Ph | allyl |
| 20b | Me | 4-MeO₂C—Ph | bond | H | bond | 4-F—Ph | allyl |
| 21b | Me | 1,4-C₆H₄ | bond | c-Pr | bond | 4-F—Ph | HOCH₂CH₂CH₂ |
| 22b | Me | 4-MeO2C—Ph | bond | H | bond | 4-F—Ph | HOCH₂CH₂CH₂ |
| 23b | Et | 4-Br—Ph | bond | H | bond | 4-F—Ph | allyl |
| 24b | Me | 1,4-C₆H₄ | bond | 2,4-diF—Ph | bond | 4-F—Ph | H₂NCH₂CH₂ |
| 25b | Me | 1,4-C₆H₄ | bond | 2,4-diF—Ph | bond | 4-F—Ph | HOCH₂CH₂CH₂ |
| 26b | Me | 1,4-C₆H₄ | bond | 2,4-diF—Ph | bond | 4-F—Ph | MeCH(OH)CH₂ |
| 27b | Me | 1,4-C₆H₄ | bond | 2,4-diF—Ph | bond | 4-F—Ph | MeC(=O)CH₂ |
| 28b | Me | 1,4-C₆H₄ | bond | 2,4-diF—Ph | bond | 4-F—Ph | HOC(Me)₂CH₂ |
| 29b | Me | 1,4-C₆H₄ | bond | 2,4-diF—Ph | bond | 4-F—Ph | MeOCH₂CH₂ |
| 30b | Me | 1,4-C₆H₄ | bond | 2,4-diF—Ph | bond | 4-F—Ph | MeNHC(=O)NHCH₂CH₂ |
| 31b | Me | 4-Br—Ph | bond | H | bond | 4-F—Ph | HOCH₂CH₂ |
| 32b | Me | 4-Br—Ph | bond | H | bond | 4-F—Ph | HOCH₂CH(OH)CH₂ |
| 33b | Me | 1,4-C₆H₄ | bond | 2,4-diF—Ph | bond | 4-F—Ph | H₂NCOCH₂CH₂ |
| 34b | Me | 1,4-C₆H₄ | bond | 2,4-diF—Ph | bond | 4-F—Ph | MeNHC(=O)CH₂CH₂ |
| 35b | Me | 1,4-C₆H₄ | bond | 2,4-diF—Ph | bond | 4-F—Ph | MeCONHCH₂CH₂ |
| 36b | Me | 1,4-C₆H₄ | bond | 2,4-diF—Ph | bond | 4-F—Ph | MeNHC(=O)OCH₂CH₂ |
| 37b | Me | 1,4-C₆H₄ | bond | 2,4-diF—Ph | bond | 4-F—Ph | H₂NSO₂NHCH₂CH₂ |
| 38b | Me | 1,4-C₆H₄ | bond | 2,4-diF—Ph | bond | 4-F—Ph | H₂NSO₂OCH₂CH₂ |
| 39b | Me | 1,4-C₆H₄ | bond | 2,4-diF—Ph | bond | 4-F—Ph | (HO)₂P(=O)OCH₂CH₂ |
| 40b | Me | 1,4-C₆H₄ | bond | 2,4-diF—Ph | bond | 4-F—Ph | H₂NCH₂C(=O)NHCH₂CH₂ |
| 41b | Me | 4-HOCH₂—Ph | bond | H | bond | 4-F—Ph | HOCH₂CH₂CH₂ |
| 42b | Me | 4-HOC(Me)₂—Ph | bond | H | bond | 4-F—Ph | allyl |
| 43b | Me | 4-Br—Ph | bond | H | bond | 2-thienyl | allyl |
| 44b | Me | 1,4-C₆H₄ | bond | 4-F—Ph | bond | Ph | HOCH₂CH₂ |
| 45b | Me | 1,4-C₆H₄ | bond | 4-F—Ph | bond | 2-thienyl | allyl |
| 46b | Me | 1,4-C₆H₄ | bond | 4-F—Ph | bond | Ph | HOCH₂CH₂CH₂ |
| 47b | Me | 1,4-C₆H₄ | bond | 2,4-diF—Ph | bond | Ph | HOCH₂CH₂ |
| 48b | Me | 1,4-C₆H₄ | bond | 2,4-diF—Ph | bond | 2-thienyl | allyl |
| 49b | Me | 1,4-C₆H₄ | bond | 4-F—Ph | bond | 2-thienyl | HOCH₂CH₂CH₂ |
| 50b | Me | 1,4-C₆H₄ | bond | 4-F—Ph | bond | 2-thienyl | MeCH(OH)CH₂ |
| 51b | Me | 1,4-C₆H₄ | bond | 4-F—Ph | bond | Ph | HOCH₂CH(OH)CH₂ |
| 52b | Me | 1,4-C₆H₄ | bond | 2,4-diF—Ph | bond | Ph | HOCH₂CH₂ |
| 53b | Me | 1,4-C₆H₄ | bond | 2,4-diF—Ph | bond | Ph | MeCH(OH)CH2 |
| 54b | Me | 1,4-C₆H₄ | bond | 2,4-diF—Ph | bond | 2-thienyl | HOCH₂CH₂CH₂ |
| 55b | Me | 1,4-C₆H₄ | bond | 2,4-diF—Ph | bond | 4-F—Ph | NCCH₂CH₂ |
| 56b | Me | 1,4-C₆H₄ | bond | 2,4-diF—Ph | bond | Ph | HOCH₂CH(OH)CH₂ |
| 57b | Et | 1,4-C₆H₄ | bond | 2,4-diF—Ph | bond | 4-F—Ph | HOCH₂CH₂ |
| 58b | Me | 1,4-C₆H₄ | bond | 2,4-diF—Ph | bond | 4-F—Ph | HOC(=O)CH₂CH₂ |
| 59b | Me | 1,4-C₆H₄ | bond | 2,4-diF—Ph | bond | 4-F—Ph | HOCH₂CH₂NHCH₂CH₂ |
| 60b | Me | 1,4-C₆H₄ | bond | 2,4-diF—Ph | bond | 4-F—Ph | HOCH₂C(=O)NHCH₂CH₂ |
| 61b | Me | 1,4-C₆H₄ | bond | 2,4-diF—Ph | bond | 4-F—Ph | MeOC(=O)NHCH₂CH₂ |
| 62b | Me | 1,4-C₆H₄ | bond | 2,4-diF—Ph | bond | 4-F—Ph | 2-(4-morpholino)ethyl |
| 63b | Me | 1,4-C₆H₄ | bond | 2,4-diF—Ph | bond | 4-F—Ph | EtNHCONHCH₂CH₂ |

TABLE 2-continued

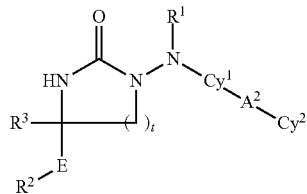

I** t = 1, 2 or 3

| Cpd. No. | R¹ | Cy¹ᵃ | A² | Cy² | E | R² | R³ |
|---|---|---|---|---|---|---|---|
| 64b | Me | 1,4-C₆H₄ | bond | 2,4-diF—Ph | bond | 4-F—Ph | MeNHC(=NCN)NHCH₂CH₂ |
| 65b | Me | 1,4-C₆H₄ | bond | 2,4-diF—Ph | bond | 4-F—Ph | MeSO2NHCH₂CH₂CH₂ |
| 66b | Me | 4-Cl—Ph | bond | H | bond | i-Pr | HOCH₂CH₂CH₂ |
| 67b | Me | 4-Me—Ph | bond | H | bond | 4-F—Ph | allyl |
| 68b | Me | 4-MeO—Ph | bond | H | bond | Ph | HOCH₂CH₂ |
| 69b | Me | 4-MeO—Ph | bond | H | bond | 4-F—Ph | allyl |
| 70b | Me | 4-HOCH₂—Ph | bond | H | bond | Ph | HOCH₂CH₂CH₂ |
| 71b | Me | 4-MeO—Ph | bond | H | bond | 4-F—Ph | HOCH₂CH₂ |
| 72b | Me | 4-Cl—Ph | bond | H | bond | 4-F—Ph | allyl |
| 73b | Me | c-hex | bond | H | bond | Ph | HOCH₂CH(OH)CH₂ |
| 74b | Me | 4-HOCH₂CH₂—Ph | bond | H | bond | Ph | HOCH₂CH₂CH₂ |
| 75b | Me | 4-MeOCH₂—Ph | bond | H | bond | Ph | HOCH₂CH₂CH₂ |
| 76b | Me | 4-Br—Ph | bond | H | bond | i-Pr | HOCH₂CH₂CH₂ |
| 77b | Me | 4-Cl—Ph | bond | H | bond | 4-F—Ph | HOCH₂CH₂CH₂ |
| 78b | Me | 4-Cl—Ph | bond | H | bond | 4-F—Ph | MeCH(OH)CH₂ |
| 79b | Me | 4-Br—Ph | bond | H | bond | Ph | allyl |
| 80b | Me | 1,4-C₆H₄ | bond | 3-pyridyl | bond | Ph | HOCH₂CH₂ |
| 81b | Me | 4-MeO—Ph | bond | H | bond | 4-F—Ph | HOCH₂CH(OH)CH₂ |
| 82b | Me | 1,4-C₆H₄ | bond | 2,4-diF—Ph | bond | i-Pr | HOCH2CH2 |
| 83b | Me | 1,4-C₆H₄ | bond | 2,4-diF—Ph | bond | 4-F—Ph | MeSO₂NHCH₂CH₂ |
| 84b | Me | 1,4-C₆H₄ | bond | 4-pyridyl | bond | Ph | HOCH₂CH₂CH₂ |
| 85b | Me | 1,4-C₆H₄ | bond | 3-pyridyl | bond | Ph | HOCH₂CH₂CH₂ |
| 86b | Me | 1,4-C₆H₄ | bond | 2,4-diF—Ph | bond | i-Pr | HOCH₂CH₂CH₂ |
| 87b | Me | 1,4-C₆H₄ | bond | 3-pyridyl | bond | 4-F—Ph | HOCH2CH2 |
| 88b | Me | 1,4-C₆H₄ | bond | 2-thienyl | bond | Ph | HOCH₂CH₂CH₂ |
| 89b | Me | 1,4-C₆H₄ | bond | 4-morpholinyl | bond | 4-F—Ph | allyl |
| 90b | Me | 1,4-C₆H₄ | bond | 4-F—Ph | bond | 2-thienyl | HOCH₂CH₂ |
| 91b | Me | 1,4-C₆H₄ | bond | 4-F—Ph | bond | Ph | NCCH₂CH₂ |
| 92b | Et | 4-Br—Ph | bond | H | bond | Ph | HOCH₂CH₂CH₂ |
| 93b | Me | 1,4-C₆H₄ | bond | 2-oxo-5-(1,2-dihydropyridyl) | bond | Ph | HOCH₂CH₂CH₂ |
| 94b | Me | 1,4-C₆H₄ | bond | 1-oxo-3-pyridyl | bond | Ph | HOCH₂CH₂CH₂ |
| 95b | Me | 1,4-C₆H₄ | bond | 2,4-diF—Ph | bond | i-Pr | HOCH₂CH(OH)CH₂ |
| 96b | Me | 1,4-C₆H₄ | bond | 4-F—Ph | bond | Ph | MeCH(OH)CH₂ |
| 97b | Me | 1,4-C₆H₄ | bond | 3-pyridyl | bond | 4-F—Ph | HOCH2CH2CH2 |
| 98b | Me | 1,4-C₆H₄ | bond | 2,4-diF—Ph | bond | Ph | Pr |
| 99b | Me | 4-Br—Ph | bond | H | bond | 4-F—Ph | HOCH₂CH₂CH₂ |
| 100b | Me | 1,4-C₆H₄ | bond | 2,4-diF—Ph | bond | 4-F—Ph | MeSO₂CH₂CH₂ |
| 101b | Me | 1,4-C₆H₄ | bond | 5-Me-1,3,4-thiadiazol-2-yl | bond | 4-F—Ph | allyl |
| 102b | Me | 1,4-C₆H₄ | bond | 4-F—Ph | bond | 2-thienyl | HOCH₂CH₂CH₂ |
| 103b | Me | 1,4-C₆H₄ | bond | 2,4-diF—Ph | bond | 2-thienyl | HOCH₂CH₂ |
| 104b | Me | 1,4-C₆H₄ | bond | 4-F—Ph | bond | Ph | H₂NCOCH₂CH₂ |
| 105b | Me | 1,4-C₆H₄ | bond | 2-MeO-5-pyridyl | bond | Ph | HOCH₂CH₂CH₂ |
| 106b | Me | 1,4-C₆H₄ | bond | 3-pyridyl | bond | 4-F—Ph | HOCH₂CH₂CH₂ |
| 107b | Et | 1,4-C₆H₄ | bond | 4-F—Ph | bond | Ph | HOCH₂CH₂CH₂ |
| 108b | Me | 1,4-C₆H₄ | bond | 4-F—Ph | bond | Ph | HOC(Me)₂CH₂ |
| 109b | Et | 4-Br—Ph | bond | H | bond | Ph | HOCH₂CH(OH)CH₂ |
| 110b | Me | 4-Br—Ph | bond | H | bond | 4-F—Ph | H₂NCOCH₂CH₂ |
| 111b | Et | 4-Br—Ph | bond | H | bond | 4-F—Ph | HOCH₂CH₂CH₂ |
| 112b | Me | 1,4-C₆H₄ | bond | 2,4-diF—Ph | bond | 4-F—Ph | NCCH₂ |
| 113b | Me | 1,4-C₆H₄ | bond | 2,4-diMe-5-thiazolyl | bond | 4-F—Ph | allyl |
| 114b | Me | 1,4-C₆H₄ | bond | 4-F—Ph | bond | 4-F—Ph | HOCH₂CH₂CH₂ |
| 115b | Me | 1,4-C₆H₄ | bond | 4-F—Ph | bond | 2-F—Ph | HOCH₂CH₂CH₂ |
| 116b | Me | 1,4-C₆H₄ | bond | 4-F—Ph | bond | 3-F—Ph | HOCH₂CH₂CH₂ |
| 117b | Me | 1,4-C₆H₄ | bond | 4-F—Ph | bond | Ph | HOC(Me)₂CH₂CH₂ |
| 118b | Me | 1,4-C₆H₄ | bond | 5-MeCO-2-thienyl | bond | Ph | HOCH₂CH₂CH₂ |
| 119b | Me | 1,4-C₆H₄ | bond | 2,4-diF—Ph | bond | Ph | H₂NCOCH₂CH₂ |
| 120b | Me | 1,4-C₆H₄ | bond | 5-(H₂NCHMe)-2-thienyl | bond | Ph | HOCH₂CH₂CH₂ |
| 121b | Et | 1,4-C₆H₄ | bond | 4-F—Ph | bond | 4-F—Ph | HOCH₂CH₂CH₂ |
| 122b | Et | 1,4-C₆H₄ | bond | 2,4-diF—Ph | bond | Ph | HOCH₂CH₂CH₂ |

TABLE 2-continued

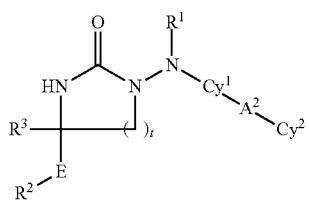

t = 1, 2 or 3

| Cpd. No. | R¹ | Cy¹ ᵃ | A² | Cy² | E | R² | R³ |
|---|---|---|---|---|---|---|---|
| 123b | Me | 1,4-C₆H₄ | bond | 5-(HOCHMe)-2-thienyl | bond | Ph | HOCH₂CH₂CH₂ |
| 124b | Et | 4-Br—Ph | bond | H | bond | 4-F—Ph | HOCH₂CH(OH)CH₂ |
| 125b | Me | 1,4-C₆H₄ | bond | 2,4-diF—Ph | bond | 4-F—Ph | H2NCH₂CH₂CH₂ |
| 126b | Me | 1,4-C₆H₄ | bond | 2,4-diF—Ph | bond | 4-F—Ph | MeNHCH₂CH₂ |
| 127b | Me | 1,4-C₆H₄ | bond | 3-(CF₃)-1-pyrazolyl | bond | 4-F—Ph | allyl |
| 128b | Me | 1,4-C₆H₄ | bond | 2,4-diF—Ph | bond | Ph | HOC(Me)₂CH₂CH₂ |
| 129b | Et | 1,4-C₆H₄ | bond | 2,4-diF—Ph | bond | 4-F—Ph | HOCH₂CH₂CH₂ |
| 130b | Me | 1,4-C₆H₄ | bond | 2,4-diF—Ph | bond | 4-F—Ph | MeSCH₂CH₂ |
| 131b | Me | Ph | bond | 2,4-diF—Ph | bond | 4-F—Ph | H₂NCOCH₂CH₂ |
| 132b | Me | 1,4-C₆H₄ | bond | 2,4-diF—Ph | bond | 4-F—Ph | H₂NCOCH₂CH₂ |
| 133b | Me | 1,4-C₆H₄ | bond | 2,4-diF—Ph | bond | 4-F—Ph | HOCH₂CH₂OCH₂CH₂ |
| 134b | Me | 1,4-C₆H₄ | bond | 2,4-diF—Ph | bond | 4-F—Ph | 2-(1-imidazolyl)ethyl |
| 135b | Me | 1,4-C₆H₄ | bond | 2,4-diF—Ph | bond | 4-F—Ph | MeCONMeCH₂CH₂ |
| 136b | Me | 1,4-C₆H₄ | bond | 4-F—Ph | bond | Ph | MeSO₂NHCH₂CH₂CH₂ |
| 137b | Me | 1,4-C₆H₄ | bond | 2,4-diF—Ph | bond | 4-F—Ph | H₂NC(=O)NHCH₂CH₂CH₂ |
| 138b | Me | 1,4-C₆H₄ | bond | 2,4-diF—Ph | bond | 4-F—Ph | H₂NC(=O)OCH₂CH₂CH₂ |
| 139b | Me | 1,4-C₆H₄ | bond | 2,4-diF—Ph | bond | 4-F—Ph | 2-(1-aminoimidazol-1-yl)ethyl |
| 140b | Me | 1,4-C₆H₄ | bond | 2,4-diF—Ph | bond | 4-F—Ph | MeNHC(=O)NHCH₂CH₂CH₂ |
| 141b | Me | 1,4-C₆H₄ | bond | 2,4-diF—Ph | bond | 4-F—Ph | H₂NC(=O)NHCH₂CH(OH)CH₂ |
| 142b | Me | 1,4-C₆H₄ | bond | 4-F—Ph | bond | 4-F—Ph | MeSO₂NHCH₂CH(OH)CH₂ |
| 143b | Me | 1,4-C₆H₄ | bond | 4-F—Ph | bond | 4-F—Ph | MeSO₂NMeCH₂CH(OH)CH₂ |
| 144b | Me | 1,4-C₆H₄ | bond | 6-CF₃-3-pyridyl | bond | 4-F—Ph | HOCH₂CH₂CH₂ |
| 145b | Me | 4-MeO—Ph | bond | H | bond | Ph | HOCH₂CH₂CH₂ |
| 146b | Me | 3-F—Ph | bond | H | bond | 4-F—Ph | HOCH₂CH₂CH₂ |
| 147b | Me | 2-F—Ph | bond | H | bond | 4-F—Ph | HOCH₂CH₂CH₂ |
| 148b | Me | 4-F—Ph | bond | H | bond | 4-F—Ph | HOCH₂CH₂CH₂ |
| 149b | Me | 4-MeO—Ph | bond | H | bond | Ph | HOCH₂CH(OH)CH₂ |
| 150b | Me | 4-Cl—Ph | bond | H | bond | Ph | H₂NCOCH₂CH₂ |
| 151b | Me | 4-MeO—Ph | bond | H | bond | 4-F—Ph | H₂NCOCH₂CH₂ |
| 152b | Me | 4-F₂HCO—Ph | bond | H | bond | 4-F—Ph | allyl |
| 153b | Me | Ph | bond | 3-pyrazolyl | bond | Ph | HOCH₂CH₂CH₂ |
| 154b | Me | 1,4-C₆H₄ | bond | 5-F-3-pyridyl | bond | Ph | allyl |
| 155b | Me | 3-CF₃—Ph | bond | H | bond | 4-F—Ph | HOCH₂CH₂CH₂ |
| 156b | Me | 4-CF₃—Ph | bond | H | bond | 4-F—Ph | HOCH₂CH₂CH₂ |
| 157b | Me | 1,4-C₆H₄ | bond | 3-pyridyl | bond | Ph | HOCH₂CH₂CH₂ |
| 158b | Me | 1,4-C₆H₄ | bond | 4-pyridyl | bond | Ph | HOCH₂CH₂CH₂ |
| 159b | Me | 1,4-C₆H₄ | bond | 4-F—Ph | bond | Ph | HOCH₂CH₂CH₂ |
| 160b | Me | 1,4-C₆H₄ | bond | 5-F-3-pyridyl | bond | Ph | HOCH₂CH₂CH₂ |
| 161b | Me | 4-MeO—Ph | bond | H | bond | 4-F—Ph | MeSO₂NHCH₂CH₂ |
| 162b | Me | 1,4-C₆H₄ | bond | 5-F-3-pyridyl | bond | 4-F—Ph | HOCH₂CH₂CH₂ |
| 163b | Me | 1,4-C₆H₄ | bond | 4-F—Ph | bond | Ph | NCC(Me)2CH2 |
| 164b | Me | 1,4-C₆H₄ | bond | 6-MeO-3-pyridyl | bond | Ph | H₂NCOCH₂CH₂ |
| 165b | Me | 1,4-C₆H₄ | bond | 5-MeO-3-pyridyl | bond | 4-F—Ph | HOCH₂CH₂CH₂ |
| 166b | Me | 1,4-C₆H₄ | bond | 5-Cl-3-pyridyl | bond | 4-F—Ph | HOCH₂CH₂CH₂ |
| 167b | Me | 1,4-C₆H₄ | bond | 3-pyridyl | bond | Ph | MeSO₂NHCH₂CH₂ |
| 168b | Me | 4-F₂HCO—Ph | bond | H | bond | 4-F—Ph | HOCH₂CH₂CH₂ |
| 169b | Me | 1,4-C₆H₄ | bond | 4-F—Ph | bond | Ph | (HO)₂P(=O)OCH₂CH₂CH₂ |
| 170b | Me | 1,4-C₆H₄ | bond | 2-Me-4-pyridyl | bond | 4-F—Ph | HOCH₂CH₂CH₂ |
| 171b | Me | 4-(HOC(Me)₂CH₂—Ph | bond | H | bond | Ph | HOCH₂CH₂CH₂ |
| 172b | Me | 1,4-C₆H₄ | bond | 1-Me-6-oxo-3-(1,6-dihydropyridyl) | bond | Ph | HOCH₂CH₂CH₂ |

TABLE 2-continued

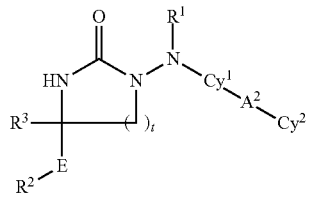

t = 1, 2 or 3

| Cpd. No. | R¹ | Cy¹ ᵃ | A² | Cy² | E | R² | R³ |
|---|---|---|---|---|---|---|---|
| 173b | Me | 4-MeO—Ph | bond | H | bond | 4-F—Ph | MeSO$_2$NHCH$_2$CH$_2$CH$_2$ |
| 174b | Me | 4-MeO—Ph | bond | H | bond | Ph | H$_2$NCOCH$_2$CH$_2$ |
| 175b | Me | 4-F—Ph | bond | H | bond | 4-F—Ph | H$_2$NCOCH$_2$CH$_2$ |
| 176b | Me | c-hex | bond | H | bond | 4-F—Ph | H$_2$NCOCH$_2$CH$_2$ |
| 177b | Me | c-hex | bond | H | bond | 4-F—Ph | MeSO$_2$NHCH$_2$CH$_2$CH$_2$ |

ᵃ Cy¹ = 1,3-C$_6$H$_4$ means 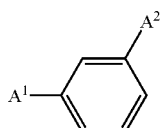

Cy¹ = 1,4-C$_6$H$_4$ means 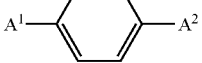

Cy¹ = 1,3-(4-F)C$_6$H$_3$ means 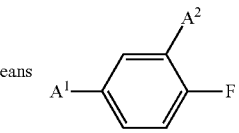

Cy¹ = 2,6-(5-Cl)-pyridyl means 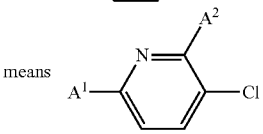

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore.

The invention includes a therapeutic method for treating or ameliorating an 11β-HSD1 mediated disorder in a subject in need thereof comprising administering to a subject in need thereof an effective amount of a compound of Formula I, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phosphatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula (I)

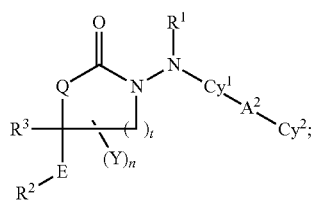

wherein:

$R^1$ is (a) hydrogen or (b) is selected from $(C_1-C_6)$alkyl, $(C_2-C_6)$alkenyl, $(C_2-C_6)$alkynyl or $(C_1-C_3)$alkoxy$(C_1-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$Cy^1$ is aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl and oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

t is 2;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl and oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$ cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$) cycloalkylalkanesulfonyl, halo($C_1$-$C_6$) alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$) alkoxy, halo($C_1$-$C_6$)alkoxy($C_1$-$C_6$)alkoxy, ($C_1$-$C_6$) alkoxycarbonyl, $H_2NCO$, $H_2NSO_2$, ($C_1$-$C_6$) alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$) alkylcarbonylamino, ($C_1$-$C_6$)alkylcarbonylamino ($C_1$-$C_6$)alkyl, ($C_1$-$C_6$)alkylsulfonylamino, ($C_1$-$C_6$) alkylsulfonylamino($C_1$-$C_6$)alkyl, ($C_1$-$C_6$) alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$) alkylamino($C_2$-$C_6$)alkoxy, di($C_1$-$C_6$)alkylamino($C_2$-$C_6$)alkoxyl and ($C_1$-$C_6$)alkylcarbonyl;

$R^3$ is selected from hydrogen, ($C_1$-$C_6$)alkyl, ($C_2$-$C_6$)alkenyl, ($C_2$-$C_6$)alkynyl and ($C_1$-$C_3$)alkoxy($C_1$-$C_3$) alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

Q is O; and $R^4$ is independently selected from H, ($C_1$-$C_6$)alkyl, halo ($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$) alkyl, hydroxy($C_1$-$C_6$)alkyl and ($C_1$-$C_6$)alkoxy($C_1$-$C_6$)alkyl;

or a pharmaceutically acceptable salt, enantiomer or diastereomer thereof.

2. The compound of claim 1, wherein
$Cy^1$ is phenyl, naphthyl, indanyl, tetrahydronaphthalene, 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, (all of which may be optionally substituted), cyclopropyl, cyclobutyl, cyclopentyl, cyclohexyl, cycloheptyl, cyclooctyl, pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide or isothiazolidine 1,1-dioxide, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$) alkynyl, ($C_3$-$C_6$)cycloalkyl($C_2$-$C_4$)alkynyl, halo($C_1$-$C_6$) alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$) cycloalkylalkoxy, halo($C_1$-$C_6$)alkoxy, halo($C_3$-$C_6$) cycloalkoxy, halo($C_4$-$C_7$)cycloalkylalkoxy, ($C_1$-$C_6$) alkylthio, ($C_3$-$C_6$)cycloalkylthio, ($C_4$-$C_7$) cycloalkylalkylthio, halo($C_1$-$C_6$)alkylthio, halo($C_3$-$C_6$) cycloalkylhio, halo($C_4$-$C_7$)cycloalkylalkylthio, ($C_1$-$C_6$) alkanesulfinyl, ($C_3$-$C_6$)cycloalkanesulfinyl, ($C_4$-$C_7$) cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo ($C_1$-$C_6$)alkanesulfonyl, halo($C_3$-$C_6$) cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;

E is a bond or ($C_1$-$C_3$)alkylene optionally substituted with 1 to 4 groups independently selected from methyl, ethyl, trifluoromethyl and oxo; and $R^3$ is selected from hydrogen, ($C_1$-$C_6$)alkyl, ($C_2$-$C_6$)alkenyl and ($C_2$-$C_6$)alkynyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo) and heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

3. The compound of claim 2, wherein the compound is of Formula (Ic):

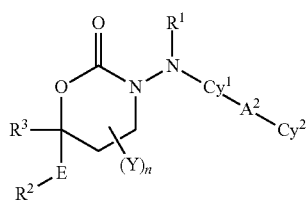

or a pharmaceutically acceptable salt, enantiomer or diastereomer thereof.

4. The compound of claim 1, wherein:
$R^1$ is hydrogen, methyl or ethyl;
$Cy^1$ is phenyl, cyclopropyl, cyclohexyl, pyrrolidinyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;
$A^2$ is a bond, O, $OCH_2CO$ or C=O;
$Cy^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

n is 0;

t is 2;

E is a bond or $CH_2$;

$R^2$ is isopropyl, thienyl, phenyl, or pyridyl, each optionally substituted with halo, methyl, methylthio or (4-morpholino)methyl; and $R^3$ is hydrogen, methyl, ethyl, propyl, butyl, vinyl, allyl or ethoxyethyl, each optionally substituted with up to two groups independently selected from HO—, MeO—, $H_2N$—, MeC(=O)NH—, MeS(=O)$_2$NH—, $H_2NC(=O)$—, MeNHC(=O)—, $HO_2C$—, $(HO)_2P(=O)O$—, $H_2NS(=O)_2O$—, $H_2NS(=O)_2NH$—, MeNHC(=O)NH—, MeNHC(=O)O-oxo, cyano, $HO_2C$—, $HOCH_2CH_2NH$—, 4-morpholino, $HOCH_2C(=O)NH$—, $H_2NCH_2C(=O)NH$—, EtNHC(=O)NH, MeOC(=O)NH—, MeNHC(=NC=N)NH—, Me-, MeS—, $MeSO_2$-$MeSO_2N(Me)$-, MeS(=O)$_2$NHC(=O)—, imidazolylamino-, imidazolyl, tetrazolyl, $H_2NCONH$—, $H_2NCO_2$—, $HOCH_2CH_2O$—, MeNH—, $Me_2N$— and MeCONMe;

or a pharmaceutically acceptable salt, enantiomer or diastereomer thereof.

5. The compound of claim 2, wherein the compound is of Formula (Ie):

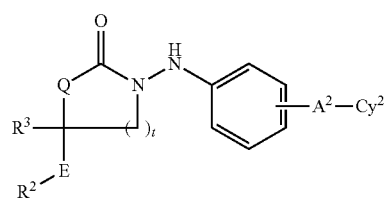

or a pharmaceutically acceptable salt, enantiomer or diastereomer thereof.

6. The compound of claim 2, wherein the compound is of Formula (If):

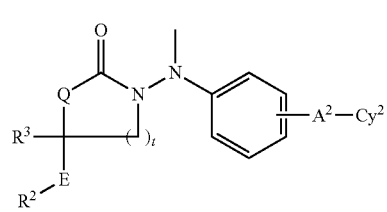

or a pharmaceutical acceptable salt, enantiomer or diastereomer thereof.

7. The compound of claim 2, wherein the compound is of Formula (Ig):

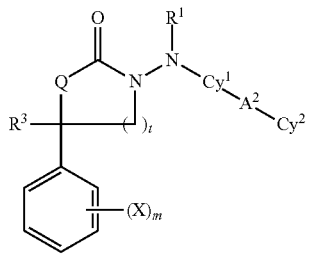

wherein:
m is 0, 1, 2, 3 or 4; and
X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
or a pharmaceutically acceptable salt, enantiomer or diastereomer thereof.

8. The compound of claim 2, wherein the compound is of Formula (Ih):

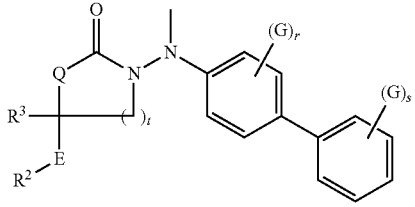

wherein:
r and s are independently 0, 1, 2, 3 or 4; and
$G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
or a pharmaceutically acceptable salt, enantiomer or diastereomer thereof.

9. The compound of claim 2, wherein the compound is of Formula (II):

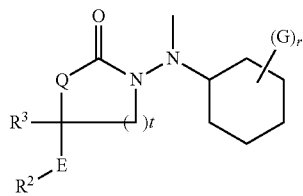

wherein:
r is 0, 1, 2, 3 or 4; and
G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino $(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
or a pharmaceutically acceptable salt, enantiomer or diastereomer thereof.

10. 6-allyl-6-(4-fluorophenyl)-3-(methyl(phenyl)amino)-1,3-oxazinan-2-one or a pharmaceutically acceptable salt, enantiomer or diastereomer thereof.

11. A method of treating a subject with a disease or disorder selected from diabetes mellitus, obesity, metabolic syndrome, prothrombotic state, proinflammatory state, glucose intolerance, hyperglycemia, hypertension, hyperlipidemia, insulin resistance, dyslipidemia, atherosclerosis, lipodystrophy, osteoporosis, glaucoma, Cushing's syndrome, Addison's disease, visceral fat obesity associated with glucocorticoid therapy, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X, comprising the step of administering to the subject an effective amount of the compound of claim 1.

12. A pharmaceutical composition comprising: i) a pharmaceutically acceptable carrier or diluent; and ii) the compound of claim 1.

13. A pharmaceutical composition comprising 6-allyl-6-(4-fluorophenyl)-3-(methyl(phenyl)amino)-1,3-oxazinan-2-one, or a pharmaceutically acceptable salt, enantiomer or diastereomer thereof; and a pharmaceutically acceptable carrier or diluent.

14. A method of treating a subject with a disease or disorder selected from diabetes mellitus, obesity, metabolic syndrome, prothrombotic state, proinflammatory state, glucose intolerance, hyperglycemia, hypertension, hyperlipidemia, insulin resistance, dyslipidemia, atherosclerosis, lipodystrophy, osteoporosis, glaucoma, Cushing's syndrome, Addison's disease, visceral fat obesity associated with glucocorticoid therapy, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X, comprising the step of administering to the subject an effective amount of 6-allyl-6-(4-fluorophenyl)-3-(methyl(phenyl)amino)-1,3-oxazinan-2-one, or a pharmaceutically acceptable salt, enantiomer or diastereomer thereof.

15. The method of claim 11, wherein the disease is diabetes mellitus.

16. The method of claim 14, wherein the disease is diabetes mellitus.

* * * * *

UNITED STATES PATENT AND TRADEMARK OFFICE
CERTIFICATE OF CORRECTION

PATENT NO. : 8,592,409 B2
APPLICATION NO. : 12/863634
DATED : November 26, 2013
INVENTOR(S) : David A. Claremon et al.

Page 1 of 1

It is certified that error appears in the above-identified patent and that said Letters Patent is hereby corrected as shown below:

In the Claims

Column 66, Claim 9, line 55, delete "(II)" and insert --(Ii)--.

Signed and Sealed this
Twentieth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,592,409 B2  Page 1 of 1
APPLICATION NO. : 12/863634
DATED : November 26, 2013
INVENTOR(S) : Claremon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 362 days.

Signed and Sealed this
Twenty-second Day of September, 2015

Michelle K. Lee
*Director of the United States Patent and Trademark Office*